United States Patent [19]

Sanemitsu et al.

[11] 4,297,129
[45] Oct. 27, 1981

[54] 3,5-DIOXO-1,2,4-TRIAZINES

[75] Inventors: Yuzuru Sanemitsu; Masato Mizutani; Seizo Sumida; Haruhiko Katoh, all of Hyogo; Hiromichi Oshio, Osaka; Shunichi Hashimoto, Sonehigashimachi, all of Japan

[73] Assignee: Sumitomo Chemical Company, Limited, Osaka, Japan

[21] Appl. No.: 143,549

[22] Filed: Apr. 25, 1980

[30] Foreign Application Priority Data

| Apr. 27, 1979 | [JP] | Japan | 54-52968 |
| Aug. 9, 1979 | [JP] | Japan | 54-102074 |
| Aug. 17, 1979 | [JP] | Japan | 54-105442 |
| Aug. 17, 1979 | [JP] | Japan | 54-105443 |
| Aug. 20, 1979 | [JP] | Japan | 54-106482 |
| Oct. 30, 1979 | [JP] | Japan | 54-140915 |
| Nov. 1, 1979 | [JP] | Japan | 54-142539 |
| Nov. 5, 1979 | [JP] | Japan | 54-143551 |
| Dec. 7, 1979 | [JP] | Japan | 54-159455 |
| Dec. 13, 1979 | [JP] | Japan | 54-162305 |
| Dec. 19, 1979 | [JP] | Japan | 54-166240 |
| Jan. 14, 1980 | [JP] | Japan | 55-2958 |
| Jan. 24, 1980 | [JP] | Japan | 55-7544 |

[51] Int. Cl.³ .................. C07D 253/06; A01N 43/64
[52] U.S. Cl. ............................ 71/93; 544/182; 544/112; 260/243.3
[58] Field of Search ............ 71/93; 544/182, 112; 260/243.3

[56] References Cited

U.S. PATENT DOCUMENTS

| 3,905,971 | 9/1975 | Miller | 544/182 |
| 3,912,723 | 10/1975 | Miller | 544/182 |

FOREIGN PATENT DOCUMENTS

| 1003218 | 2/1957 | Fed. Rep. of Germany | 544/182 |
| 1337112 | 7/1963 | France | 544/182 |
| 40-6239 | 3/1965 | Japan | 544/182 |

Primary Examiner—John M. Ford
Attorney, Agent, or Firm—Birch, Stewart, Kolasch & Birch

[57] ABSTRACT

Use of 3,5-dioxo-1,2,4-triazine derivatives of the formula:

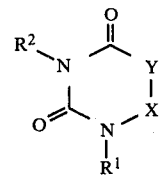

wherein X, Y, $R^1$ and $R^2$ are each as defined in the specification, as a herbicidal agent exerting a strong controlling and preventing effect against wild oats without any material phytotoxicity to wheat.

20 Claims, No Drawings

3,5-DIOXO-1,2,4-TRIAZINES

The present invention relates to 3,5-dioxo-1,2,4-triazine derivatives and their use and production. More particularly, it relates to 3,5-dioxo-1,2,4-triazine derivatives showing a strong exterminating activity on wild oats, herbicidal compositions containing them and processes for preparing them.

The said 3,5-dioxo-1,2,4-triazine derivatives are representable by the formula:

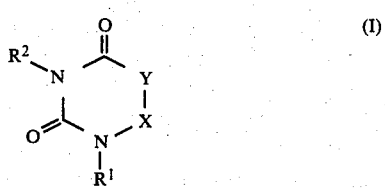

wherein (1) -X-Y- represents —N=CH—, $R^1$ is a hydrogen atom, a hydroxylmethyl group, an aminomethyl group of the formula:

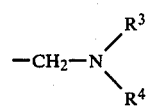

(in which $R^3$ and $R^4$ are each hydrogen, $C_1$-$C_{12}$ alkyl, allyl, propargyl, cyanoethyl, phenyl or $C_3$-$C_{10}$ cycloalkyl or, when taken together with the adjacent nitrogen atom, represent a 3 to 13-membered saturated nitrogen-containing heterocyclic group optionally containing an oxygen atom or an additional nitrogen atom and/or optionally bearing not more than three methyl or ethyl groups), an acyloxymethyl group of the formula: —CH$_2$—OOC—R$^5$ (in which $R^5$ is $C_1$-$C_9$ alkyl, $C_2$-$C_5$ alkenyl, $C_2$-$C_5$ alkynyl or cyclohexyl, these being optionally substituted with not more than 5 halogen, $C_1$-$C_5$ alkoxy, phenyl or phenoxy groups, or phenyl, naphthyl, nicotinyl or isonicotinyl, these being optionally substituted with not more than 5 methyl, methoxy, halogen, nitro or trihalomethyl groups or with 3,4-methylenedioxy) or a cyclic ether group of the formula:

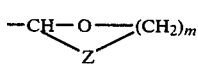

(in which Z is —CH$_2$CH$_2$— and m is an integer of 1 or 2 or Z is —CHX'CH$_2$—, —CHX'CHX'— or —CH=CH— (X' being halogen) and m is an integer of 1) and $R^2$ is a hydrogen atom, an aminomethyl group of the formula:

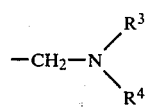

(in which $R^3$ and $R^4$ are each as defined above) or a cyclic ether group of the formula:

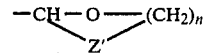

(in which Z' is —CH$_2$CH$_2$— and n is an integer of 1 or 2 or Z is —CHY'CH$_2$— (Y' being halogen) and n is an integer of 1), provided that when $R^2$ is a hydrogen atom, $R^1$ is a hydroxymethyl group, an acyloxymethyl group of the formula: —CH$_2$—OOC—R$^5$ or a cyclic ether group of the formula:

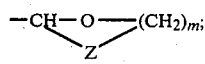

when $R^2$ is an aminomethyl group of the formula:

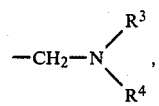

$R^1$ is an aminomethyl group of the formula:

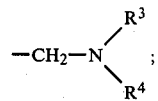

or when $R^2$ is a cyclic ether group of the formula:

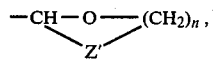

$R^1$ is a hydrogen atom or a group of the formula:

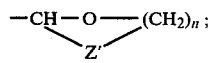

or (2) —X—Y— represents —NH—CH$_2$—, $R^1$ is a hydrogen atom, an acyloxymethyl group of the formula: —CH$_2$—OOC—R$^6$ (in which $R^6$ is $C_1$-$C_9$ alkyl, cyclohexyl or phenyl, these being optionally substituted with not more than 5 methyl, methoxy, fluorine, chlorine or trihalomethyl groups or with 3,4-methylenedioxy) or a cyclic ether group of the formula:

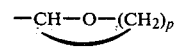

(in which p is an integer of 3 or 4) and $R^2$ is a hydrogen atom or a cyclic ether group of the formula:

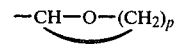

(in which p is as defined above), provided that when $R^2$ is a cyclic ether group of the formula:

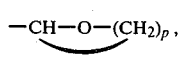

$R^1$ is a hydrogen atom or a cyclic ether group of the formula:

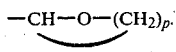

In any event, the cyclic ether group of the formula:

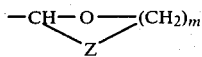

can not be

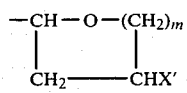

and the cyclic ether group of the formula:

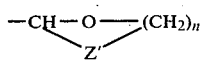

can not be

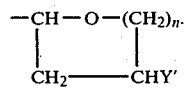

In recent years, rampant growth of wild oats in the culture fields of wheat and barley is considered as a serious problem due to the remarkable decrease in the crop yields resulting therefrom (D. P. Jones et al.: Wild Oats in World Agriculture (1976)). Since wild oats are the plants of Gramineae to which wheat belongs and they are similar to each other ecologically and morphologically, particularly at the stage before earing, it is not easy to exterminate wild oats only.

In extermination of wild oats in the culture field of wheat, the control and prevention should be effected at the initial stage of the growth of wheat so as to avoid a decrease in the crop yield. Further, the application of an effective herbicide should be carried out around the completion of the germination of wild oats, because their germination is somewhat uneven. For these necessities, the appearance of a highly selective herbicide, which is suitable for over-the-top foliar treatment at the initial stage of the growth of wheat and which can control and prevent the growth of wild oats without causing any material injury to wheat, has been highly demanded.

As the result of an extensive study, it has now been found that the 3,5-dioxo-1,2,4-triazine derivatives (I) in the free or salt form exert a strong herbicidal action on wild oats with a high selectivity to wheat.

As the compounds structurally similar to the 3,5-dioxo-1,2,4-triazine derivatives (I), there are known 3,5-dioxo-2-methyl-2,3,4,5-tetrahydro-1,2,4-triazine (hereinafter referred to as "Control (a)") as described in German patent 2,028,552 and 3,5-dioxo-2,3,4,5-tetrahydro-1,2,4-triazine (hereinafter referred to as "Control (b)") as described in U.S. Pat. No. 3,116,994.

In the said German patent, it is stated that Control (a) controls the growth of plants and is useful as a plant growth regulator. It is also stated that 3,5-dioxo-2-propyl-2,3,4,5-tetrahydro-1,2,4-triazine (hereinafter referred to as "Control (c)") is stronger than Control (a) in the controlling activity. The comparative test carried out by the present inventors revealed that the 3,5-dioxo-1,2,4-triazine derivatives (I) are much more potent than Controls (a) and (c) in the herbicidal activity against wild oats, barnyard grass, raddish, cucumber, etc.

The said U.S. patent states that Control (b) shows a growth inhibitory activity against plants and is useful as a plant growth regulator. The comparative test conducted by the present inventors revealed that both of the 3,5-dioxo-1,2,4-triazine derivatives (I) and Control (b) show a remarkable herbicidal activity against wild oats. However, on over-the-top foliar treatment, the 3,5-dioxo-1,2,4-triazine derivatives (I) do not produce any material phytotoxicity onto Gramineae crop plants such as wheat, while Control (b) does produce a severe phytotoxicity.

Also, the 3,5-dioxo-1,2,4-triazine derivatives (I) show a notable herbicidal activity in soil treatment before emergence. For instance, they can exterminate morningglory, wild oats, etc. without causing any injury onto cotton, rice, sugarbeet, wheat, etc. Their residual effect for a long period of time is notable. In addition to culture fields, they may be applied to orchards, forests, lawns, nonculture fields, etc. for the herbicidal purpose. Since they have a growth controlling activity on various kinds of plants, their use at sufficiently low concentrations can suppress the growth of lawn and garden plants without causing any phytotoxicity.

In the 3,5-dioxo-1,2,4-triazine derivatives of the formula (I), there are included structurally known and novel compounds. Known are those of the formula (I) wherein (a) —X—Y— is —N=CH—, $R^1$ is hydroxymethyl and $R^2$ is a potassium atom; (b) —X—Y— is —N=CH—, $R^1$ is hydroxymethyl and $R^2$ is a hydrogen atom; (c) —X—Y— is —N=CH—, $R^1$ is

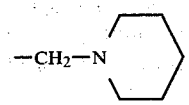

and $R^2$ is

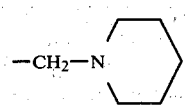

(d) —X—Y— is —N=CH—, $R^1$ is —CH$_2$OOC—CH$_3$ and $R^2$ is a hydrogen atom; (e) —X—Y— is —N=CH—, $R^1$ is

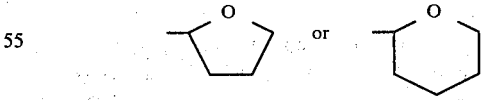

and $R^2$ is a hydrogen atom; and (f) —X—Y— is —NH—CH$_2$—, $R^1$ is a hydrogen atom and $R^2$ is a hydrogen atom. However, the biological activity of these compounds has not been known. The others are novel compounds.

The 3,5-dioxo-1,2,4-triazine derivatives (I) may be in the free or salt form. Examples of the salt form include alkali metal salts, alkaline earth metal salts, amine salts, etc. When, however, both of $R^1$ and $R^2$ are hydrogen, only $R^2$ can take a salt form.

Specific examples of the 3,5-dioxo-1,2,4-triazine derivatives (I) which are novel are as follows:

| Compound No. | Chemical structure | Physical property |
|---|---|---|
| 1 | Na—N, CH₂OH substituent | Melting point, >300° C. |
| 2 | Li—N, CH₂OH substituent | Softening temp., 155–165° C. |
| 3 | Ca salt, (CH₂OH)₂ | Glass foam decomp. temp., >300° C. |
| 4 | Na—N, NH, H · 2H₂O | Softening temp., 122.3° C. |
| 5 | Li—N, NH, H · H₂O | Melting point, 252–257° C. (decomp.) |
| 6 | Ca salt, NH, H · 4H₂O | Melting point, >300° C. |
| 7 | diethylamino-methyl derivative | $n_D^{28.0}$ 1.5075 |
| 8 | dipropargyl derivative | $n_D^{27.5}$ 1.5415 |
| 9 | dipropylamino derivative | Softening temp., 62–72° C. |
| 10 | butyl-ethylamino derivative | $n_D^{26.5}$ 1.4910 |
| 11 | diallylamino derivative | $n_D^{25.5}$ 1.5225 |
| 12 | phenyl-ethylamino derivative | Melting point, 132.6° C. |
| 13 | tetra(n-C₁₂H₂₅) derivative | Melting point, 34.0–36.0° C. |
| 14 | cyclohexyl-methylamino derivative | $n_D^{29.0}$ 1.5262 |
| 15 | butyl-methylamino derivative | $n_D^{23.5}$ 1.4960 |
| 16 | dihexyl or piperidyl derivative | $n_D^{24.5}$ 1.4850 |

| Compound No. | Chemical structure | Physical property |
|---|---|---|
| 17 | 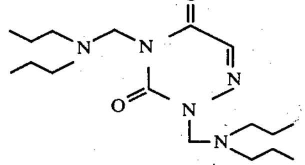 | $n_D^{24.5}$ 1.4920 |
| 18 | 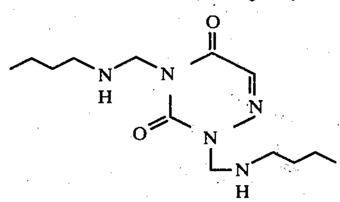 | Softening temp., 37–42° C. |
| 19 | 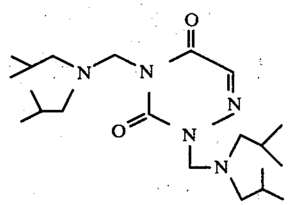 | $n_D^{25.5}$ 1.4845 |
| 20 | 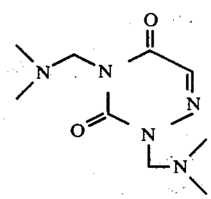 | $n_D^{27.0}$ 1.5189 |
| 21 | 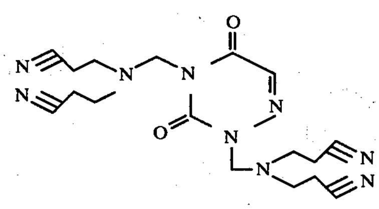 | Melting point, 78.2° C. |
| 22 | 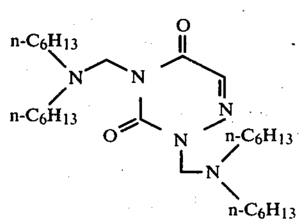 | $n_D^{27.0}$ 1.4775 |
| 23 | 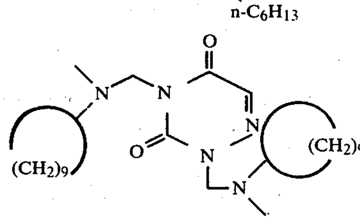 | $n_D^{25.5}$ 1.5285 |
| 24 | 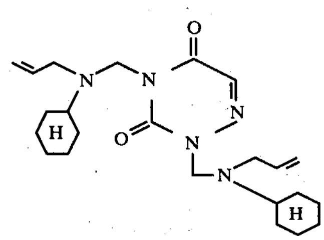 | $n_D^{27.5}$ 1.5320 |
| 25 | | $n_D^{25.5}$ 1.5386 |
| 26 | | $n_D^{27.5}$ 1.4840 |
| 27 | | $n_D^{25.5}$ 1.4775 |
| 28 | | $n_D^{25.0}$ 1.4765 |
| 29 | | $n_D^{22.5}$ 1.4990 |
| 30 | | $n_D^{27.5}$ 1.5400 |
| 31 | | Melting point, 134.1° C. |

-continued

| Compound No. | Chemical structure | Physical property |
|---|---|---|
| 32 | (piperidine with C2H5)-N-CH2-[triazinedione]-CH2-N-(piperidine with C2H5) | $n_D^{27.0}$ 1.5255 |
| 33 | piperidine-N-CH2-[triazinedione]-CH2-N-piperidine | Melting point, 86.1° C. |
| 34 | (4-methylpiperidine)-N-CH2-[triazinedione]-CH2-N-(4-methylpiperidine) | Melting point, 144.7° C. |
| 35 | [(CH2)12 ring]-N-CH2-[triazinedione]-CH2-N-[(CH2)12 ring] | $n_D^{26.5}$ 1.5250 |
| 36 | (2-methylpiperidine)-N-CH2-[triazinedione]-CH2-N-(2-methylpiperidine) | Melting point, 51.5° C. |
| 37 | morpholine-N-CH2-[triazinedione]-CH2-N-morpholine | Melting point, 140.4° C. |

-continued

| Compound No. | Chemical structure | Physical property |
|---|---|---|
| 38 | (2,6-dimethylmorpholine)-N-CH2-[triazinedione]-CH2-N-(2,6-dimethylmorpholine) | Melting point, 115.9° C. |
| 39 | (4-methylpiperazine)-N-CH2-[triazinedione]-CH2-N-(4-methylpiperazine) | Melting point, 141.3° C. |
| 40 | HN-[triazinedione]-N-CH2OCCH2CH3 (with C=O) | Melting point, 119.3° C. |
| 41 | HN-[triazinedione]-N-CH2-O-C(=O)-(3-methylphenyl) | Melting point, 139.9° C. |
| 42 | HN-[triazinedione]-N-CH2-O-C(=O)-(4-methylphenyl) | Melting point, 139.3° C. |
| 43 | HN-[triazinedione]-N-CH2-O-C(=O)-naphthyl | Melting point, 134.0° C. |
| 44 | Na-N-[triazinedione]-N-CH2-O-C(=O)-naphthyl | Melting point, 201.1° C. (decomp.) |

| Compound No. | Chemical structure | Physical property |
|---|---|---|
| 45 | (triazine with N-CH₂OCCH₂CH₃, C=O) | Melting point, 111.4° C. |
| 46 | (triazine with N-CH₂OCCH₂CH₂CH₃, C=O) | Melting point, 112.1° C. |
| 47 | (triazine with N-CH₂OC-C(CH₃)₃, C=O) | Melting point, 113.6° C. |
| 48 | (triazine with N-CH₂OC(CH₂)₈CH₃, C=O) | Melting point, 117.3° C. |
| 49 | (triazine with N-CH₂OC(CH₂)₄CH₃, C=O) | Melting point, 126.0° C. |
| 50 | (triazine with N-CH₂OC(=O)-phenyl) | Melting point, 134–135° C. |
| 51 | (triazine with N-CH₂OC(=O)-C₆H₄-NO₂) | Melting point, 216–217° C. |
| 52 | (triazine with N-CH₂OC(=O)-C₆H₄-Cl (para)) | Melting point, 198–200° C. |
| 53 | (triazine with N-CH₂OC(=O)-CH=CH-Cl) | Melting point, 152–153° C. |
| 54 | (triazine with N-CH₂OC(=O)-C₆H₄-Br) | Melting point, 219.0° C. |
| 55 | (triazine with N-CH₂OC(=O)-C₆H₃-2,4-Cl₂) | Melting point, 206.2° C. |
| 56 | (triazine with N-CH₂OC(=O)-C₆H₄-OCH₃ (ortho)) | Melting point, 140.3° C. |
| 57 | (triazine with N-CH₂OC(=O)-C₆H₄-OCH₃ (para)) | Melting point, 104.4° C. |
| 58 | (triazine with N-CH₂OC(=O)-pyridyl) | Melting point, 222.0° C. |

-continued

| Compound No. | Chemical structure | Physical property |
|---|---|---|
| 59 | (structure with pyridine-3-yl) | Melting point, 175–177° C. |
| 60 | (structure with 2-naphthyl) | Melting point, 138.8° C. |
| 61 | (structure with 3,4-dichlorophenyl) | Melting point, 210.7° C. |
| 62 | (structure with 4-fluorophenyl) | Melting point, 169.9° C. |
| 63 | (structure with CH₂OCCH₂O-phenyl) — CH$_2$OCCH$_2$O–C$_6$H$_5$ | Melting point, 97.6° C. |
| 64 | (structure with CH$_2$OCCH$_2$–C$_6$H$_5$) | Melting point, 154.6° C. |
| 65 | (structure with CH$_2$OCCH=CH–C$_6$H$_5$) | Melting point, 138.1° C. |

-continued

| Compound No. | Chemical structure | Physical property |
|---|---|---|
| 66 | (structure with 3-CF$_3$-phenyl) | Melting point, 191.9° C. |
| 67 | (structure with 3,4-methylenedioxyphenyl) | Melting point, 180.2° C. |
| 68 | (structure with CH$_2$OCC(CH$_3$)=CH$_2$) | Melting point, 140–141° C. |
| 69 | (structure with CH$_2$OCCH$_2$CH(CH$_3$)$_2$) | Melting point, 84.7° C. |
| 70 | (structure with CH$_2$OCCH=C(CH$_3$)$_2$) | Melting point, 116.3° C. |
| 71 | (structure with CH$_2$OC–cyclohexyl) | Melting point, 95.3° C. |
| 72 | (structure with NH–CH$_2$OCCH$_3$) | $n_D^{24.5}$ 1.5008 |

-continued

| Compound No. | Chemical structure | Physical property |
|---|---|---|
| 73 | [structure: triazine with CH2OC(O)-C6H4-CH3 (para)] | Melting point, 163.5° C. |
| 74 | [structure: Na-N triazine with CH2OC(O)-C6H4-CH3 (para)] | Melting point, 225–235° C. (decomp.) |
| 75 | [structure: triazine with CH2OC(O)-C6H5] | Melting point, 167.9° C. |
| 76 | [structure: triazine with CH2OC(O)-C6H4-OCH3 (para)] | Melting point, 161.1° C. |
| 77 | [structure: triazine with CH2OC(CH2)4CH3, O] | Melting point, 85.3° C. |
| 78 | [structure: triazine with CH2OC(O)-cyclohexyl H] | Melting point, 128.3° C. |
| 79 | [structure: triazine with CH2OC(O)-C6H4-F (para)] | Melting point, 174.4° C. |
| 80 | [structure: Na-N triazine with tetrahydropyran] | Melting point, 160–162° C. |
| 81 | [structure: triazine with dihydrofuran] | Melting point, 147–148° C. |
| 82 | [structure: triazine with dichloro-tetrahydrofuran] | Melting point, 174–175° C. |
| 83 | [structure: triazine with dibromo-tetrahydrofuran] | Melting point, 190–192° C. |
| 84 | [structure: Na-N triazine with dihydrofuran] | Melting point, 208–215° C. |
| 85 | [structure: triazine with two tetrahydrofuran groups] | Melting point, 67–68° C. |
| 86 | [structure: triazine with tetrahydrofuran, NH] | Melting point, 87° C. |

-continued

| Compound No. | Chemical structure | Physical property |
|---|---|---|
| 87 | 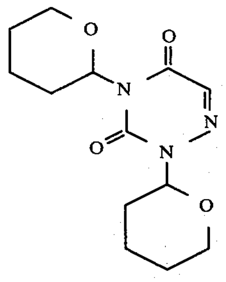 | Melting point, 32° C. |
| 88 | 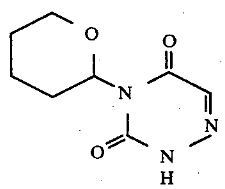 | Melting point, 116° C. |
| 89 | 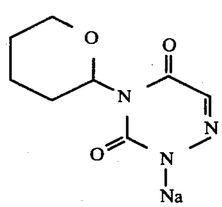 | Melting point, 160–165° C. |
| 90 | 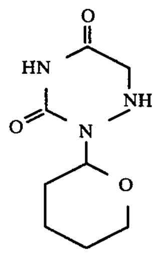 | Melting point, 205–206° C. |

-continued

| Compound No. | Chemical structure | Physical property |
|---|---|---|
| 91 | 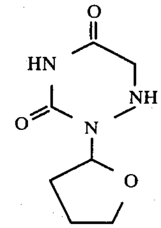 | Melting point, 197° C. |
| 92 | 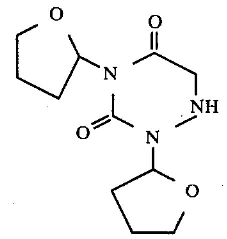 | Melting point, 169° C. |
| 93 | 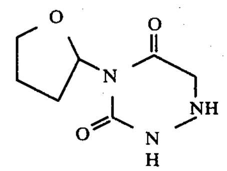 | Melting point, 136–138° C. |
| 94 | 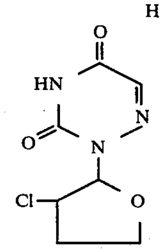 | Melting point, 157–158° C. |

Specific examples of the 3,5-dioxo-1,2,4-triazine derivatives (I) which are known are as follows:

| Compound No. | Chemical structure | Literature |
|---|---|---|
| 95 | 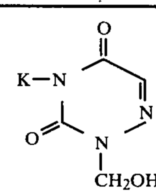 | M.Prystas et al.: Collection Czechoslov. Chem. Commum., 36, 81 (1965) |
| 96 | 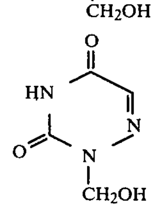 | M.Prystas et al.: Collection Czechoslov. Chem. Commum., 36, 81 (1965) |
| 97 | 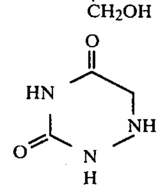 | J.Gut et al.: Collection Czechoslov. Chem. Commum., 26, 974 (1961) |

| Compound No. | Chemical structure | Literature |
|---|---|---|
| 98 | 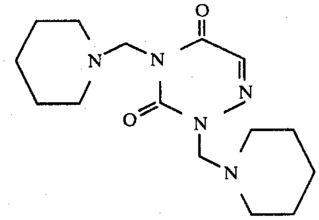 | S. Asano et al.: YAKUGAKU ZASSHI, 92, 1162 (1972) |
| 99 | 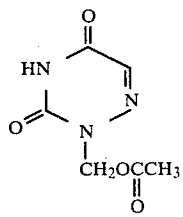 | M. Prystas et al.: Collection Czechoslov. Chem. Commum., 36, 81 (1965) |
| 100 | 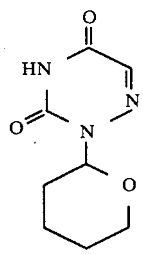 | S. Hillers et al.: Izyskaniya Protivo-oepukholevykh Prep., 3, 109 (1968) |
| 101 | 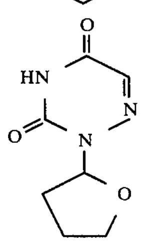 | S. Hillers et al.: Izyskaniya Protivo-oepukholevykh Prep., 3, 109 (1968) |

The 3,5-dioxo-1,2,4-triazine derivatives (I) can be produced by various procedures, of which some typical ones are shown below.

Procedure 1

The 3,5-dioxo-1,2,4-triazine derivatives (I) wherein —X—Y— is —N=CH—, $R^1$ is

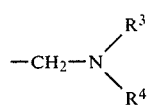

and $R^2$ is

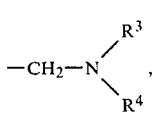

which correspond to the following formula:

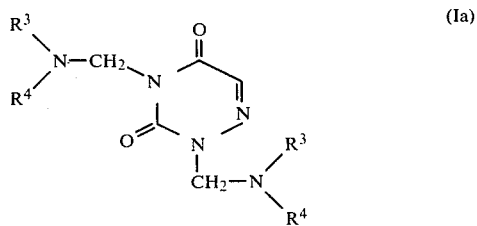

wherein $R^3$ and $R^4$ are each as defined above, can be produced by reacting 3,5-dioxo-2,3,4,5-tetrahydro-1,2,4-triazine of the formula:

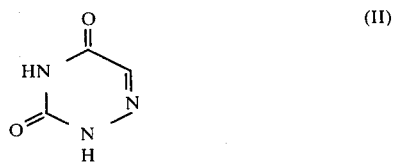

with formaldehyde or its chemical equivalent and an amine of the formula:

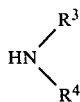 (III)

wherein $R^3$ and $R^4$ are each as defined above.

As the chemical equivalent of formaldehyde, there may be used those which can release formaldehyde under the reaction conditions. Specific examples are formalin, paraformaldehyde, s-trioxane, etc. The molar proportion of the starting compound (II), the formaldehyde or its chemical equivalent and the amine (III) to be subjected to the reaction is usually 1:2–4:2–4, preferably 1:2–2.5:2–2.5. the reaction may be carried out in the presence or absence of an inert solvent (e.g. water, methanol, ethanol, isopropanol, ethylene glycol). The reaction is usually accomplished at a temperature of 20° to 150° C., preferably of 40° to 100° C., within a period of 10 minutes to 20 hours.

Procedure 2

The 3,5-dioxo-1,2,4-triazine derivatives (I) wherein —X—Y— is —N=CH—, $R^1$ is —CH$_2$—OOC—$R^5$ and $R^2$ is a hydrogen atom, which correspond to the following formula:

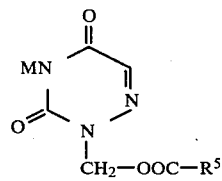 (Ib)

wherein M is hydrogen, alkali metal or alkaline earth metal and $R^5$ is as defined above, can be produced by reacting 2-hydroxymethyl-3,5-dioxo-2,3,4,5-tetrahydro-1,2,4-triazine or its salt of the formula:

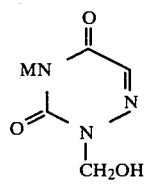 (IV)

wherein M is as defined above, with a carboxylic acid of the formula:

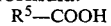
$R^5$—COOH (V)

wherein $R^5$ is as defined above, or its reactive derivative at the carboxyl group.

The starting compound (IV) may be subjected to the reaction in its free or salt form. In case of the salt form, there may be used the alkali metal salt (e.g. sodium salt, potassium salt, lithium salt) or the alkaline earth metal salt (e.g. calcium salt). As the reactive derivative of the carboxylic acid (V), there are exemplified the acid halide, the acid anhydride, etc.

When the reaction is carried out between the starting compound (IV) and the carboxylic acid (V) itself, there is usually employed a condensing agent (e.g. N,N-dicyclohexylcarbodiimide) in the presence of an inert solvent (e.g. chloroform, benzene, toluene, xylene, dimethylsulfoxide, dimethylformamide, pyridine). The reaction is accomplished usually at a temperature of 0° to 50° C., preferably of 15° to 30° C., within a period of 10 minutes to 24 hours.

When the reaction is carried out between the starting compound (IV) and the acid halide or acid anhydride of the carboxylic acid (V), there is usually employed a base (e.g. trimethylamine, triethylamine, pyridine) in the presence or absence of an inert solvent (e.g. methylene dichloride, chloroform, carbon tetrachloride, benzene, toluene, xylene, diethyl ether, dimethoxyethane, dimethylformaldehyde, dimethylsulfoxide, pyridine). The reaction is perfected normally at a temperature of 0° to 50° C., preferably of 15° to 30° C., within a period of 10 minutes to 24 hours.

Procedure 3

The 3,5-dioxo-1,2,4-triazine derivatives (I) wherein —X—Y— is —N=CH—, $R^1$ is —H or

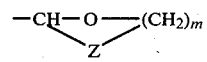

(wherein Z is —CH$_2$CH$_2$— and m is an integer of 1 or 2 or Z is —CHX'CH$_2$— (X' being halogen) and m is an integer of 1) and $R^2$ is —H or

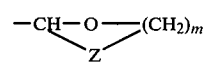

(wherein Z and m are each as defined above), provided that when $R^2$ is —H, $R^1$ is

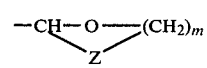

(in which Z is —CHX'CH$_2$— and m is an integer of 1), which correspond to the following formulae:

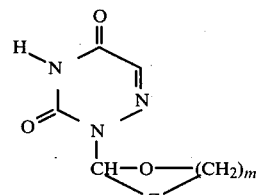 (Ic)

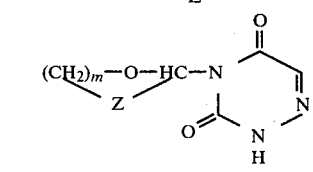 (Ic')

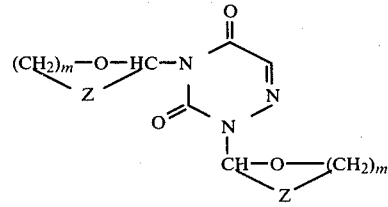 (Ic")

wherein Z and m are each as defined above, can be produced by reacting 3,5-bis(trimethylsilyloxy)-1,2,4-triazine of the formula:

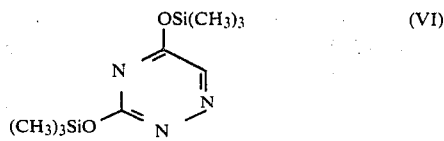

with a cyclic ether derivative of the formula:

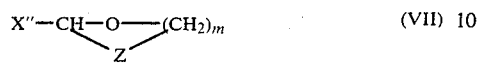

wherein X" is halogen (e.g. chlorine, bromine), lower alkoxy (e.g. methoxy, ethoxy, propoxy, butoxy), substituted or unsubstituted phenoxy (e.g. p-nitrophenoxy) or lower alkanoyloxy (e.g. acetyloxy, propionyloxy), and Z and m are each as defined above.

The starting bis(trimethylsilyloxy) compound (VI) is obtainable by silylating 3,5-dioxo-2,3,4,5-tetrahydro-1,2,4-triazine with trimethylchlorosilane according to a conventional procedure (W. W. Zorbach: Synthetic Procedure in Nucleic Acid Chemistry, Vol. 1, page 347 (1968)).

As the cyclic ether derivative (VII), there are exemplified 2-acetoxytetrahydrofuran, 2-methoxytetrahydrofuran, 2-t-butoxytetrahydrofuran, 2-chlorotetrahydrofuran, 2-(p-nitrophenoxy)tetrahydrofuran, 2,3-dichlorotetrahydrofuran, 2-acetoxytetrahydropyran, 2-methoxytetrahydropyran, 2-chlorotetrahydropyran, 2-(p-nitrophenoxy)tetrahydropyran, etc.

The reaction between the bis(trimethylsilyloxy) compound (VI) and the cyclic ether derivative (VII) is usually carried out in an inert solvent (e.g. dichloromethane, dimethylformamide), if necessary, in the presence of a catalyst such as a Lewis acid. The molar ratio of the bis(trimethylsilyloxy) compound (VI) and the cyclic ether derivative (VII) to be subjected to the reaction may be from 1:1 to 1:3. Examples of the Lewis acid are tin tetrachloride, boron trifluoride etherate, aluminum trichloride, zinc chloride, titanium tetrachloride, etc. The reaction is achieved usually at a temperature of −50° to 100° C., preferably of 0° to 25° C., within a period of 1 to 24 hours, preferably of 15 to 24 hours.

As the reaction product, there is obtained a mixture of $N^2$-monosubstituted, $N^4$-monosubstituted and $N^2,N^4$-disubstituted compounds, which may be separated by a per se conventional procedure such as chromatography into each component. Among the said components, the $N^2$-monosubstituted compound is the most easily produced, and then the $N^4$-monosubstituted compound is produced. The $N^2,N^4$-disubstituted compound is the most difficulty produced derivative so that when the production of such disubstituted compound is desired, a higher temperature and a longer time are needed.

Procedure 4

The 3,5-dioxo-1,2,4-triazine derivatives (I) wherein —X—Y— is —N=CH—, $R^1$ is

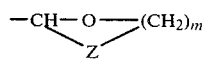

(wherein m is 1 and Z is —CHX'CHX'— or —CH=CH—) and $R^2$ is —H, which correspond to the following formula:

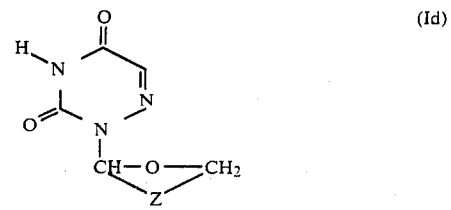

wherein Z is —CHX'CHX'— or —CH=CH—, can be produced by subjecting the $N^2$-monosubstituted compound of the formula:

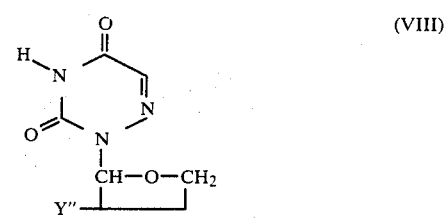

wherein Y" is halogen (e.g. chlorine, bromine) to dehydrohalogenation to give $N^2$-(2,5-dihydro-2-furanyl)-3,5-dioxo-2,3,4,5-tetrahydro-1,2,4-triazine of the formula:

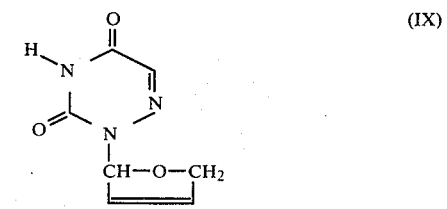

followed by halogenation of the latter to give the $N^2$-(3,4-dihalotetrahydro-2-furanyl)-3,5-dioxo-2,3,4,5-tetrahydro-1,2,4-triazine of the formula:

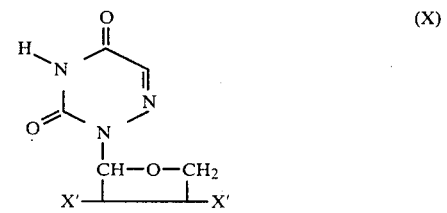

wherein X' is as defined above.

The starting $N^2$-monosubstituted compound (VIII) is obtainable in Procedure 3 as explained above.

The dehydrohalogenation may be carried out by reacting the $N^2$-monosubstituted compound (VIII) with a dehydrohalogenating agent such as an alkali hydroxide (e.g. sodium hydroxide, potassium hydroxide), an alkali hydride (e.g. sodium hydride, potassium hydride) or an alkali alkoxide (e.g. sodium methoxide, potassium t-butoxide) in an inert solvent (e.g. water, methanol, ethanol, propanol, butanol, dimethylformamide, dimethylsulofixde) at a temperature of 20° to 80° C. for a period of 3 to 6 hours.

The halogenation is usually carried out by reacting the thus produced $N^2$-(2,5-dihydro-2-furanyl)-3,5-dioxo-2,3,4,5-tetrahydro-1,2,4-triazine (IX) with a halogen (e.g. bromine, chlorine) in an aprotic solvent (e.g. carbon tetrachloride, chloroform, toluene) at a temperature of −5° to 10° C. for a period of 2 to 4 hours.

Procedure 5

The 3,5-dioxo-1,2,4-triazine derivatives of the formula (I) wherein —X—Y— is —NH—CH₂—, which correspond to the formula:

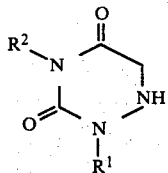

(Ie)

wherein $R^1$ and $R^2$ are each as defined above, can be produced by subjecting the corresponding 2,3,4,5-tetrahydro-1,2,4-triazine-3,5-dione compound of the formula:

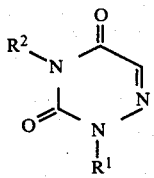

(XI)

wherein $R^1$ and $R^2$ are each as defined above to reduction.

The reduction may be effected by any per se conventional procedure suitable for hydrogenation of a double bond. Examples are catalytic hydrogenation, reduction with a metal in the presence of an acid, etc.

In case of the catalytic hydrogenation, there may be employed platinum oxide, palladium, etc. as the reduction catalyst. Examples of the reaction medium are water, organic solvents and their mixtures. Particularly preferred are water, alcohols (e.g. methanol, ethanol) or their mixtures. The reduction is usually accomplished at a temperature of 0° to 50° C. for a period of 1 to 12 hours under a pressure ranging from atmospheric pressure to 5 atm.

In case of the reduction with a metal in the presence of an acid, there may be used the combination of a metal such as zinc, iron, nickel or tin with an acid such as an organic acid (e.g. acetic acid) or an inorganic acid (e.g. hydrochloric acid, nitric acid, sulfuric acid). As the reaction medium, there may be used water, an organic solvent or their mixture, preferably water, methanol, ethanol or their mixture. The reduction is usually achieved at a temperature of 20° to 100° C. for a period of 1 to 5 hours.

Still, the application of the reduction to the 1,6-dehydro compound (XI) wherein $R^1$ or $R^2$ is a hydrogen atom but in its salt form affords the corresponding hydrogenated compound (Ie) wherein $R^1$ or $R^2$ is a hydrogen atom but in its salt form may be employed.

The 3,5-dioxo-1,2,4-triazine derivatives (I) wherein $R^1$ or $R^2$ is hydrogen can be readily converted into the corresponding salts by a per se conventional procedure, for instance, treatment with a metallizing agent or an amine.

Examples of the metallizing agent are a metal hydroxide (e.g. lithium hydroxide, sodium hydroxide, potassium hydroxide, calcium hydroxide), a metal alkoxide (e.g. sodium methoxide, sodium ethoxide, potassium t-butoxide), butyl lithium, sodium hydride, metallic magnesium, etc. Depending on the kind of the metallizing agent, the reaction medium to be used may be varied. When the metallizing agent is a metal hydroxide, water is favorably used. When the metallizing agent is a metal alkoxide, the use of alcohols is preferred. In case of the metallizing agent being butyl lithium or metallic magnesium, ethers are favorably employed. In case of the metallizing agent being sodium hydride, dimethylformamide or dimethylsulfoxide is preferably used. The treatment with the metallizing agent is usually accomplished at a temperature of 0° to 80° C., preferably of 0° to 30° C., for a period of 10 minutes to 24 hours.

Examples of the amine are isopropylamine, cyclohexylamine, diethylaniline, morpholine, triethylamine, tri-n-propylamine, aniline, etc. As the reaction medium, there may be employed methanol, ethanol, ethylene glycol or the like. The reaction proceeds usually at a temperature of 50° to 200° C., preferably of 60° to 150° C., for a period of 30 minutes to 12 hours.

As hereinabove mentioned, the salts of the 3,5-dioxo-1,2,4-triazine derivatives (I) wherein —X—Y— is —NH—CH₂— are also obtainable by reduction of the corresponding 1,6-dehydro compounds of the formula (XI) in salt forms at the 2 or 4-position.

Further, it is possible to convert the thus prepared salts into the corresponding free forms, for instance, by treatment with an acid such as an organic acid (e.g. acetic acid, formic acid) or an inorganic acid (e.g. hydrochloric acid, sulfuric acid, nitric acid, phosphoric acid) at a temperature of −70° to 50° C. for a period of several minutes to 1 hour.

The invention is further illustrated by the following detailed examples which are not intended to limit the scope thereof.

EXAMPLE 1

A mixture of 3,5-dioxo-2,3,4,5-tetrahydro-1,2,4-triazine (4.00 g), p-formaldehyde (2.33 g), diethylamine (6.21 g) and methanol (30 ml) is heated under reflux for 4 hours. The reactive mixture is cooled to room temperature, and methanol is distilled off under reduced pressure to give a pale yellow liquid, which is 2,4-bis(diethylaminomethyl)3,5-dioxo-2,3,4,5-tetrahydro-1,2,4-triazine (Compound No. 7). Yield, 9.51 g (94.9%). $n_D^{28.0}$, 1.5075.

EXAMPLE 2

A mixture of 3,5-dioxo-2,3,4,5-tetrahydro-1,2,4-triazine (2.26 g), p-formaldehyde (1.32 g), n-propylamine (2.48 g) and ethanol (30 ml) is heated under reflux for 3 hours. The reaction mixture is cooled to room temperature, and ethanol is distilled off under reduced pressure. To the resultant residue are added ethyl acetate (70 ml) and water (20 ml), and the ethyl acetate layer is separated, washed with water and concentrated in vacuo to give 2,4-bis(n-propylaminomethyl)-3,5-dioxo-2,3,4,5-tetrahydro-1,2,4-triazine (Compound No. 9) as a pale yellow liquid, which turns to glassy solids on addition of petroleum ether. Yield, 2.57 g (50.3%). Softening temperature, 62°–72° C.

EXAMPLE 3

A mixture of 3,5-dioxo-2,3,4,5-tetrahydro-1,2,4-triazine (2.00 g), p-formaldehyde (1.06 g), 3-methylpiperidine (3.51 g) and ethanol (20 ml) is heated under reflux for 4 hours. The reaction mixture is cooled to room temperature, and ethanol is removed in vacuo to give 5.84 g of 2,4-bis(3-methylpiperidin-1-yl-methyl)-3,5-dioxo-2,3,4,5-tetrahydro-1,2,4-triazine (Compound No. 31) as a pale yellow liquid, which spontaneously solidifies. The solid is recrystallized from a mixture of ethanol/n-hexane to give white crystals. Yield, 4.79 g (80.6%). M.P., 134.1° C.

EXAMPLE 4

A mixture of 2,3,4,5-tetrahydro-3,5-dioxo-1,2,4-triazine (4.00 g), p-formaldehyde (6.48 g), morpholine (3.24 g) and ethanol (30 ml) is heated under reflux for 2 hours. The reaction mixture is cooled to room temperature, and ethanol is removed in vacuo to give white crystals of 2,4-bis(morpholin-4-yl-methyl)-3,5-dioxo-2,3,4,5-tetrahydro-1,2,4-triazine (Compound No. 37), which is recrystallized from ethanol. Yield, 9.04 g (82.0%). M.P., 140.4° C.

EXAMPLE 5

2-Hydroxymethyl-3,5-dioxo-2,3,4,5-tetrahydro-1,2,4-triazine (4.00 g) and propionic anhydride (4.36 g) are dissolved in pyridine (20 ml), and the mixture is allowed to stand overnight. The pyridine is removed in vacuo, and the residue is added with ethyl acetate (70 ml) and water (20 ml). The ethyl acetate layer is separated, washed with water (20 ml) and concentrated to give white crystals of 2-propionyloxymethyl-3,5-dioxo-2,3,4,5-tetrahydro-1,2,4-triazine (Compound No. 40). Yield, 4.82 g (93%). M.P., 111.3° C.

EXAMPLE 6

2-Hydroxymethyl-3,5-dioxo-2,3,4,5-tetrahydro-1,2,4-triazine (1.00 g), p-methylbenzoic acid (0.95 g) and N,N-dicyclohexylcarbodiimide (2.90 g) are dissolved in pyridine, and the mixture is allowed to stand overnight. The reaction mixture is then evaporated to dryness to give a residue, which is extracted with chloroform. The chloroform extract is condensed to give an oil, which is purified by thin layer chromatography with silica gel and recrystallized from a mixture of ethanol/n-hexane. 2-(p-Methylbenzoyloxymethyl)-3,5-dioxo-2,3,4,5-tetrahydro-1,2,4-triazine (Compound No. 42) is thus obtained. Yield, 1.01 g (56%). M.P. 139.3° C.

EXAMPLE 7

A potassium salt of 2-hydroxymethyl-3,5-dioxo-2,3,4,5-tetrahydro-1,2,4-triazine (1.81 g) is suspended in pyridine (20 ml). The mixture is ice-cooled and dropwise added with 1-naphthylcarbonyl chloride (2.48 g). After the completion of the addition, the reaction mixture is allowed to stand overnight. The pyridine is removed in vacuo from the mixture to give the residue. The residue is dissolved in water, and the resultant aqueous solution is acidified with acetic acid. The acidic aqueous solution is added with ethyl acetate (50 ml) and water (20 ml), and the ethyl acetate layer is separated and evaporated to dryness under reduced pressure. The residue is recrystallized from ethanol to give 2-(1-naphthylcarbonyloxymethyl)-3,5-dioxo-2,3,4,5-tetrahydro-1,2,4-triazine (Compound No. 43). Yield, 1.44 g (82%). M.P., 134.0° C.

EXAMPLE 8

3,5-Dioxo-2,3,4,5-tetrahydro-1,2,4-triazine (1 g) and 2-t-butoxytetrahydrofuran (1.9 g) are dissolved in dimethylformamide (3 ml), and the mixture is stirred at 160°-165° C. for 5 hours. The dimethylformamide is removed in vacuo from the reaction mixture to give the residue. The residue is column-chromatographed over silica gel using a mixture of acetone/n-hexane (⅓) as an eluent. The first major fraction gives 2,4-bis(tetrahydro-2-furanyl)-3,5-dioxo-2,3,4,5-tetrahydro-1,2,4-triazine (Compound No. 85) (yield, 0.2 g; 12%), the second gives 3,5-dioxo-4-(tetrahydro-2-furanyl)-2,3,4,5-tetrahydro-1,2,4-triazine (Compound No. 86) (yield, 0.6 g; 36%) and the third gives 2-(tetrahydro-2-furanyl)-3,5-dioxo-2,3,4,5-tetrahydro-1,2,4-triazine (Compound No. 101) (yield, 0.4 g; 24%). Compound Nos. 85 and 86 melt at 67°-68° C. and 87° C., respectively.

EXAMPLE 9

3,5-Bis(trimethylsilyloxy)-1,2,4-triazine (2.5 g) and 2-chlorotetrahydropyran (1.8 g) are dissolved in dimethylformamide (1 ml), and the mixture is stirred overnight at room temperature and concentrated in vacuo. The residue is column-chromatographed over silica gel using a mixture of acetone/n-hexane (⅓) as an eluent. The first major fraction gives 1.0 g (40%) of 2,4-bis(tetrahydro-2-pyranyl)-3,5-dioxo-2,3,4,5-tetrahydro-1,2,4-triazine (Compound No. 87) (yield, 1.0 g; 36%), the second gives 4-(tetrahydro-2-pyranyl)-3,5-dioxo-2,3,4,5-tetrahydro-1,2,4-triazine (Compound No. 88) (yield, 0.8 g; 40%) and the third gives 2-(tetrahydro-2-pyranyl)-3,5-dioxo-2,3,4,5-tetrahydro-1,2,4-triazine (Compound No. 100) (yield, 0.6 g; 30%). Compound Nos. 87 and 88 melt at 32° C. and 116° C., respectively.

EXAMPLE 10

2-(3-Chloro-tetrahydro-2-furanyl)-3,5-dioxo-2,3,4,5-tetrahydro-1,2,4-triazine (0.8 g) and potassium t-butoxide (0.7 g) are added to dimethyl sulfoxide (3 ml), and the mixture is stirred at room temperature for 3 hours. The reaction mixture is poured into ice-water. The mixture is acidified with acetic acid and extracted with chloroform. The chloroform extract is washed with water, dried and evaporated to remove the solvent. The crude residue is recrystallized from ethanol to give 2-(2,5-dihydro-2-furanyl)-3,5-dioxo-2,3,4,5-tetrahydro-1,2,4-triazine (Compound No. 81). Yield, 0.5 g (76%). M.P., 147°-148° C.

EXAMPLE 11

2-(2,5-Dihydro-2-furanyl)-3,5-dioxo-2,3,4,5-tetrahydro-1,2,4-triazine (1 g) is dissolved in carbon tetrachloride (5 ml), and the mixture is bubbled with chlorine gas for 1 hour while cooling to 0° C. and then stirred at room temperature for another 1 hour. The reaction mixture is evaporated to dryness to give the residue, which is recrystallized from a mixture of ethyl acetate/n-hexane. 2-(3,4-Dichloro-tetrahydro-2-furanyl)-2,3,4,5-tetrahydro-1,2,4-triazine (Compound No. 82) is thus obtained. Yield, 1 g (78%). M.P., 174°-175° C.

EXAMPLE 12

2-Acetyloxymethyl-3,5-dioxo-2,3,4,5-tetrahydro-1,2,4-triazine (2.0 g) is dissolved in ethanol (100 ml), and the mixture is added with platinum oxide (400 mg) and stirred at room temperature for 4 hours in an atmosphere of hydrogen. After the completion of the reaction, the catalyst is filtered off, and the filtrate is concentrated in vacuo to give a pale yellow liquid. The liquid is purified by column chromatography over silica gel using a mixture of chloroform/methanol as an eluent to give a colorless transparent viscous liquid, which is 2-acetyloxymethyl-3,5-dioxo-hexahydro-1,2,4-triazine (Compound No. 72). Yield, 1.42 g (70.3%). $n_D^{24.5}$, 1.5008.

EXAMPLE 13

2-(4-Methylbenzoyloxymethyl)-3,5-dioxo-2,3,4,5-tetrahydro-1,2,4-triazine (2.1 g) is dissolved in ethanol (100 ml), and the mixture is added with platinum oxide (400 mg) and stirred at room temperature for 3 hours in an atmosphere of hydrogen. After the completion of the reaction, the catalyst is filtered off, and the filtrate is concentrated in vacuo to give a pale yellow liquid. The liquid is purified by chromatography over silica gel using a mixture of chloroform/methanol as an eluent to give white crystals of 2-(4-methylbenzoyloxymethyl)-3,5-dioxo-hexahydro-1,2,4-triazine (Compound No. 73). The product is recrystallized from a mixture of ethanol/n-hexane. Yield, 1.35 g (62.2%). M.P., 163.5° C.

EXAMPLE 14

$N^2$-(Tetrahydro-2-pyranyl)-3,5-dioxo-2,3,4,5-tetrahydro-1,2,4-triazine (1.9 g) and zinc (0.5 g) are added to a mixture of acetic acid (6 ml) and water (6 ml), and the mixture is heated under reflux for 5 hours. After the completion of the reaction, the reaction mixture is filtered, and the filtrate is evaporated to dryness. The residue is recrystallized from methanol to give crude $N^2$-(tetrahydro-2-pyranyl)-3,5-dioxo-hexahydro-1,2,4-triazine (Compound No. 90). Yield, 1.5 g (78%). M.P., 205°–206° C.

EXAMPLE 15

$N^2$-(Tetrahydro-2-furanyl)-3,5-dioxo-2,3,4,5-tetrahydro-1,2,4-triazine (2.5 g) is dissolved in ethanol (50 ml), and the mixture is added with platinum oxide (1 g) and stirred at room temperature for 5 hours in an atmosphere of hydrogen. After the completion of the reaction, the mixture is filtered, and the filtrate is evaporated to dryness. The residue is recrystallized from ethanol to give $N^2$-(tetrahydro-2-furanyl)-3,5-dioxo-hexahydro-1,2,4-triazine (Compound No. 91). Yield, 2.1 g (85%). M.P., 197° C.

EXAMPLE 16

Metallic sodium (84 mg) is dissolved in ethanol (50 ml). To the resultant ethanol solution of sodium ethoxide is added 2-(1-naphthylcarbonyloxymethyl)-3,5-dioxo-2,3,4,5-tetrahydro-1,2,4-triazine (1.14 g). The reaction mixture is stirred at room temperature for 6 hours, and the precipitated white crystals of 2-(1-naphthylcarbonyloxymethyl)-4-sodio-3,5-dioxo-2,3,4,5-tetrahydro-1,2,4-triazine (Compound No. 44) is filtered off. The product is thoroughly washed with ethanol (50 ml) and dried. Yield, 1.07 g (92%). M.P., 201.1° C. (decomp.).

EXAMPLE 17

2-(4-Methylbenzoyloxymethyl)-3,5-dioxo-hexahydro-1,2,4-triazine (1.0 g) is dissolved in methanol (60 ml), and the mixture is added with sodium methoxide (0.21 g) and stirred at room temperature for 30 minutes. The methanol is removed in vacuo, and the resulting white crystals are thoroughly washed with ethanol to give 2-(4-methylbenzoyloxymethyl)-3,5-dioxo-4-sodio-hexahydro-1,2,4-triazine (Compound No. 74). Yield, 0.84 g (77.8%). M.P., 225°–235° C. (decomp.).

EXAMPLE 18

3,5-Dioxo-4-sodio-2,3,4,5-tetrahydro-1,2,4-triazine monohydrate (770 mg) dissolved in water (60 ml) is hydrogenated for 4 hours in the presence of platinum oxide (100 mg) at atmospheric pressure. The catalyst is filtered off, and the filtrate is concentrated in vacuo to give a colorless transparent liquid. The liquid is dissolved in ethanol (30 ml), and the solvent is then removed in vacuo to give amorphous solids of 3,5-dioxo-4-sodio-hexahydro-1,2,4-triazine dihydrate (Compound No. 4). Yield, 850 mg (98.2%). Softening temperature, 122.3° C.

EXAMPLE 19

2-(4-Methylbenzoyloxymethyl)-3,5-dioxo-4-sodio-hexahydro-1,2,4-triazine (500 mg) as obtained in Example 17 is dissolved in 1% hydrochloric acid (15 ml). The mixture is then extracted with ethyl acetate (20 ml). The ethyl acetate extract is washed with water (5 ml), dried over anhydrous magnesium sulfate and concentrated in vacuo to give white crystals of 2-(4-methylbenzoyloxymethyl)-3,5-dioxo-hexahydro-1,2,4-triazine (Compound No. 73). Yield, 450 mg (97.8%).

In the practical usage of the 3,5-dioxo-1,2,4-triazine derivatives (I) in the free or salt form, they may be applied as such or in any preparation form such as wettable powders, emulsifiable concentrates, granules, fine granules or dusts.

In producing such preparation form, a solid or liquid carrier may be used. As for the solid carrier, there may be given mineral powders (e.g. kaolin, bentonite, clay, montmorillonite, talc, diatomaceous earth, mica, vermiculite, gypsum, calcium carbonate, apatite), vegetable powders (e.g. soybean powder, wheat flour, wooden powder, tobacco powder, starch, crystalline cellulose), high molecular weight compounds (e.g. petroleum resin, polyvinyl chloride, dammar gum, ketone resin), alumina, wax and the like.

As for the liquid carrier, there may be given alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methyl ethyl ketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ether ether), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene-oxypropylene polymers, polyoxyethylene alkyl phosphates, fatty acid salts, alkyl sulfates, alkyl sulfonates, alkylaryl sulfonates, alkyl phosphates, polyoxyethylene alkyl sulfate, quaternary ammonium salts, oxyalkylamine and the like. But, the surface active agent is not of course limited to these compounds. And, if necessary, gelatin, casein, sodium alginate, starch, agar, polyvinyl alcohol or the like may be used as an auxiliary agent.

In the preparation of a herbicidal composition, the content of the compound (I) may be from 1 to 95% by weight, preferably from 1 to 80% by weight.

The 3,5-dioxo-1,2,4-triazine derivatives (I) of the invention may be used together with other herbicides to improve their activity as herbicides, and in some cases, a synergistic effect can be expected. As the other herbicides, there may be given, for example, 1,1-dimethyl-3-(3-trifluoromethylphenyl)urea, 3-(3,4-dichlorophenyl)-1,1-dimethylurea; sodium methanearsonate, 2-(3,4-dichlorophenyl)-4-methyltetrahydro-1,2,4-oxathiazole-3,5-dione; 2-methylthio-4,6-bis(isopropylamino)-s-triazine; 3-isopropyl-1H-2,1,3-benzothiadiazine-(4)-3H-one-2,2-dioxide; 2-methyl-4-chloro-phenoxyacetic acid; S-ethyl-N,N-hexamethylenethiol-carbamate; 3,4-dichloropropionanilide; 3-(2,4-dichloro-5-isopropoxyphenyl)-5-t-butyl-1,3,4-oxadiazol-2(3H)-one; 3-(methoxycarbonylamino)phenyl-N-(3-methylphenyl)carbamate; 5-amino-4-chloro-2-phenylpyridazin-3(2H)-one; 3-cyclohexyl-5,6-trimethyleneuracil; 4-amino-4,5-dihydro-3-methyl-6-phenyl-1,2,4-triazin-5(4H)-one; 3,6-dichloro-2-methoxybenzoic acid; 3-(3-chloro-4-methylphenyl)-1,1-dimethylurea; 3-(2-benzothiazolyl)-1,3-dimethylurea; 3-(4-isopropylphenyl)-1,1-dimethylurea and the like. But, the herbicides are not of course limited to these examples.

The dosage rate of the compound (I) depends upon the kind of formulation, the sort of cultivated plant, the method of application, etc. Generally, however, the dosage rate is from 2 to 200 grams, preferably from 5 to 50 grams, of the active ingredient per are.

Practical embodiments of the herbicidal composition according to the invention are illustratively shown in the following examples wherein parts and % are by weight.

PREPARATION EXAMPLE 1

Eighty parts of Compound No. 11, 5 parts of polyoxyethylene alkylaryl ether and 15 parts of synthetic silicon oxide hydrate are well mixed while being powdered to obtain a wettable powder.

In the same manner as above, Compound No. 34, 37, 40, 72, 84, 87, 95, 98, 99 or 101 can be formulated in a wettable powder.

PREPARATION EXAMPLE 2

Thirty parts of Compound No. 8, 7 parts of polyoxyethylene alkylaryl ether, 3 parts of alkylaryl sulfonate and 60 parts of xylene are well mixed to obtain an emulsifiable concentrate.

In the same manner as above, Compound No. 30, 37, 57, 73, 81, 85, 90, 96, 98, 99 or 100 can be formulated in an emulsifiable concentrate.

PREPARATION EXAMPLE 3

One part of Compound No. 9, 1 part of white carbon, 5 parts of ligninsulfonate and 93 parts of clay are well mixed while being powdered. The mixture is then well kneaded with water, granulated and dried to obtain granules.

In the same manner as above, Compound No. 32, 39, 64, 77, 80, 82, 87, 93, 98 or 99 can be formulated in granules.

PREPARATION EXAMPLE 4

Fourty parts of bentonite, 5 parts of ligninsulfonate and 55 parts of clay are well mixed while being powdered. The mixture is then well kneaded with water, granulated and dried to obtain granules containing no active ingredient. The granules are then impregnated with 5 parts of Compound No. 9 to obtain granules.

In the same manner as above, Compound No. 31, 38, 69, 78, 83, 85, 91, 98, 99 or 100 can be formulated in granules.

PREPARATION EXAMPLE 5

Three parts of Compound No. 13, 0.5 part of isopropyl phosphate, 66.5 parts of clay and 30 parts of talc are well mixed while being powdered to obtain a dust.

In the same manner as above, Compound No. 33, 38, 53, 75, 80, 81, 89, 92, 98 or 99 can be formulated in a dust.

The application of the 3,5-dioxo-1,2,4-triazine derivatives (I) as herbicides will be illustrated in the following Examples wherein the phytotoxicity to cultivated plants and the herbicidal activity against weeds were evaluated as follows: the aereal parts of the test plants were cut off and weighed (fresh weight); the percentage of the fresh weight of the treated plant to that of the untreated plant was calculated with the latter fresh weight taken as 100; and the crop damage and the herbicidal activity were evaluated by the standard given in the table below. The rating values of phytotoxicity, 0 and 1, and those of herbicidal effect, 5, 4 and 3, are generally regarded as satisfactory to protect cultivated plants and to control weeds, respectively.

| Rating value | Fresh weight (percentage to untreated plot) (%) Cultivated plant or weed |
|---|---|
| 5 | 0 |
| 4 | 1–19 |
| 3 | 20–49 |
| 2 | 50–79 |
| 1 | 80–99 |
| 0 | 100 |

EXAMPLE 20

Post-emergence application (outdoors):

Plastic trays (diameter, 10 cm; 0.5 liter in volume) were filled with upland field soil, and the seeds of wheat and wild oat were separately sowed in the trays and grown outdoors for 20 days. The required amount of the test compound was sprayed to the foliage of the test plants over the top by means of a small hand sprayer. After the spraying, the test plants were grown outdoors for further 40 days, and herbicidal activity and phytotoxicity were examined. The results are shown in Table 1. In the above foliar application, the test compounds were each formulated into an emulsifiable concentrate, and the required amount of the emulsifiable concentrate was dispersed in water for application at a spray volume of 5 liters per are and applied with the addition of a wetting agent. At the time of application, wheat was in a 3-leaf stage and 13 to 14.5 cm in height and wild oat was in a 3-leaf stage and 8 to 13.0 cm in height, respectively.

TABLE 1

| Compound No. | Dosage (weight of active ingredient, g/are) | Phytotoxicity Wheat | Herbicidal activity Wild oat |
|---|---|---|---|
| 1 | 40 | 1 | 4 |
|   | 20 | 0 | 4 |
| 2 | 40 | 1 | 4 |
|   | 20 | 0 | 4 |
| 3 | 40 | 1 | 4 |
|   | 20 | 0 | 4 |

TABLE 1-continued

| Compound No. | Dosage (weight of active ingredient, g/are) | Phyto-toxicity Wheat | Herbicidal activity Wild oat |
|---|---|---|---|
| 4 | 40 | 1 | 4 |
|  | 20 | 0 | 4 |
| 5 | 40 | 1 | 4 |
|  | 20 | 0 | 4 |
| 6 | 40 | 1 | 4 |
|  | 20 | 0 | 4 |
| 7 | 40 | 1 | 4 |
|  | 20 | 0 | 4 |
| 8 | 40 | 1 | 4 |
|  | 20 | 0 | 4 |
| 9 | 40 | 1 | 4 |
|  | 20 | 0 | 4 |
| 10 | 40 | 1 | 4 |
|  | 20 | 0 | 4 |
| 11 | 40 | 1 | 4 |
|  | 20 | 0 | 4 |
| 12 | 40 | 1 | 4 |
|  | 20 | 0 | 4 |
| 13 | 40 | 1 | 4 |
|  | 20 | 0 | 4 |
| 14 | 40 | 1 | 4 |
|  | 20 | 0 | 4 |
| 15 | 40 | 1 | 4 |
|  | 20 | 0 | 4 |
| 16 | 40 | 1 | 4 |
|  | 20 | 0 | 4 |
| 17 | 40 | 1 | 4 |
|  | 20 | 0 | 4 |
| 18 | 40 | 1 | 4 |
|  | 20 | 0 | 4 |
| 19 | 40 | 1 | 4 |
|  | 20 | 0 | 4 |
| 20 | 40 | 1 | 4 |
|  | 20 | 0 | 4 |
| 21 | 40 | 1 | 4 |
|  | 20 | 0 | 4 |
| 22 | 40 | 1 | 4 |
|  | 20 | 0 | 4 |
| 23 | 40 | 1 | 4 |
|  | 20 | 0 | 4 |
| 24 | 40 | 1 | 4 |
|  | 20 | 0 | 4 |
| 25 | 40 | 1 | 4 |
|  | 20 | 0 | 4 |
| 26 | 40 | 1 | 4 |
|  | 20 | 0 | 4 |
| 27 | 40 | 1 | 4 |
|  | 20 | 0 | 4 |
| 28 | 40 | 1 | 4 |
|  | 20 | 0 | 4 |
| 29 | 40 | 1 | 4 |
|  | 20 | 0 | 4 |
| 30 | 40 | 1 | 4 |
|  | 20 | 0 | 4 |
| 31 | 40 | 1 | 4 |
|  | 20 | 1 | 4 |
| 32 | 40 | 1 | 4 |
|  | 20 | 1 | 4 |
| 33 | 40 | 1 | 4 |
|  | 20 | 0 | 4 |
| 34 | 40 | 1 | 4 |
|  | 20 | 0 | 4 |
| 35 | 40 | 1 | 4 |
|  | 20 | 1 | 4 |
| 36 | 40 | 1 | 4 |
|  | 20 | 0 | 4 |
| 37 | 40 | 1 | 4 |
|  | 20 | 0 | 4 |
| 38 | 40 | 0 | 4 |
|  | 20 | 0 | 4 |
| 39 | 40 | 1 | 4 |
|  | 20 | 0 | 4 |
| 40 | 40 | 1 | 4 |
|  | 20 | 0 | 4 |
| 41 | 40 | 0 | 4 |
|  | 20 | 0 | 4 |
| 42 | 40 | 0 | 4 |
|  | 20 | 0 | 4 |
| 43 | 40 | 1 | 4 |
|  | 20 | 1 | 4 |
| 44 | 40 | 1 | 4 |
|  | 20 | 1 | 4 |
| 45 | 40 | 1 | 4 |
|  | 20 | 0 | 4 |
| 46 | 40 | 0 | 4 |
|  | 20 | 0 | 4 |
| 47 | 40 | 1 | 4 |
|  | 20 | 0 | 4 |
| 48 | 40 | 1 | 4 |
|  | 20 | 0 | 4 |
| 49 | 40 | 1 | 4 |
|  | 20 | 0 | 4 |
| 50 | 40 | 0 | 4 |
|  | 20 | 0 | 4 |
| 51 | 40 | 1 | 4 |
|  | 20 | 0 | 4 |
| 52 | 40 | 0 | 4 |
|  | 20 | 0 | 4 |
| 53 | 40 | 0 | 4 |
|  | 20 | 0 | 4 |
| 54 | 40 | 0 | 4 |
|  | 20 | 0 | 4 |
| 55 | 40 | 0 | 4 |
|  | 20 | 0 | 4 |
| 56 | 40 | 0 | 4 |
|  | 20 | 0 | 4 |
| 57 | 40 | 0 | 5 |
|  | 20 | 0 | 4 |
| 58 | 40 | 0 | 4 |
|  | 20 | 0 | 4 |
| 59 | 40 | 1 | 5 |
|  | 20 | 0 | 4 |
| 60 | 40 | 0 | 4 |
|  | 20 | 0 | 4 |
| 61 | 40 | 0 | 4 |
|  | 20 | 0 | 4 |
| 62 | 40 | 0 | 4 |
|  | 20 | 0 | 4 |
| 63 | 40 | 0 | 4 |
|  | 20 | 0 | 4 |
| 64 | 40 | 1 | 5 |
|  | 20 | 0 | 4 |
| 65 | 40 | 0 | 4 |
|  | 20 | 0 | 4 |
| 66 | 40 | 0 | 4 |
|  | 20 | 0 | 4 |
| 67 | 40 | 0 | 4 |
|  | 20 | 0 | 4 |
| 68 | 40 | 1 | 4 |
|  | 20 | 0 | 4 |
| 69 | 40 | 0 | 4 |
|  | 20 | 0 | 4 |
| 70 | 40 | 1 | 4 |
|  | 20 | 0 | 4 |
| 71 | 40 | 0 | 4 |
|  | 20 | 0 | 4 |
| 72 | 40 | 1 | 4 |
|  | 20 | 0 | 4 |
| 73 | 40 | 1 | 4 |
|  | 20 | 0 | 4 |
| 74 | 40 | 1 | 4 |
|  | 20 | 0 | 4 |
| 75 | 40 | 1 | 4 |
|  | 20 | 0 | 4 |
| 76 | 40 | 1 | 4 |
|  | 20 | 0 | 4 |
| 77 | 40 | 1 | 4 |
|  | 20 | 0 | 4 |
| 78 | 40 | 1 | 4 |
|  | 20 | 0 | 4 |
| 79 | 40 | 1 | 4 |
|  | 20 | 0 | 4 |
| 80 | 40 | 1 | 4 |
|  | 20 | 0 | 4 |

TABLE 1-continued

| Compound No. | Dosage (weight of active ingredient, g/are) | Phytotoxicity Wheat | Herbicidal activity Wild oat |
|---|---|---|---|
| 81 | 40 | 1 | 4 |
|  | 20 | 0 | 3 |
| 82 | 40 | 1 | 4 |
|  | 20 | 0 | 3 |
| 83 | 40 | 1 | 4 |
|  | 20 | 1 | 4 |
| 84 | 40 | 1 | 4 |
|  | 20 | 0 | 3 |
| 85 | 40 | 1 | 4 |
|  | 20 | 0 | 3 |
| 86 | 40 | 0 | 4 |
|  | 20 | 0 | 4 |
| 87 | 40 | 1 | 4 |
|  | 20 | 1 | 4 |
| 88 | 40 | 0 | 4 |
|  | 20 | 0 | 4 |
| 89 | 40 | 0 | 4 |
|  | 20 | 0 | 4 |
| 90 | 40 | 1 | 4 |
|  | 20 | 0 | 3 |
| 91 | 40 | 1 | 4 |
|  | 20 | 0 | 3 |
| 92 | 40 | 1 | 4 |
|  | 20 | 1 | 3 |
| 93 | 40 | 1 | 4 |
|  | 20 | 0 | 4 |
| 94 | 40 | 1 | 4 |
|  | 20 | 0 | 4 |
| 95 | 40 | 1 | 4 |
|  | 20 | 0 | 4 |
| 96 | 40 | 0 | 4 |
|  | 20 | 0 | 4 |
| 97 | 40 | 1 | 4 |
|  | 20 | 0 | 4 |
| 98 | 40 | 1 | 4 |
|  | 20 | 0 | 4 |
| 99 | 40 | 1 | 4 |
|  | 20 | 0 | 4 |
| 100 | 40 | 1 | 4 |
|  | 20 | 0 | 4 |
| 101 | 40 | 1 | 4 |
|  | 20 | 0 | 4 |
| Control (a) | 40 | 1 | 1 |
|  | 20 | 1 | 0 |
| Control (b) | 40 | 4 | 4 |
|  | 20 | 4 | 4 |
| Control (c) | 40 | 1 | 2 |
|  | 20 | 1 | 2 |

EXAMPLE 21

Post-emergence application (in greenhouse):-

Wagner's pots (1/5000 are) were each filled with paddy field soil, and the seeds of barnyard grass, wild oat, radish and cucumber were separately sowed in the pots and grown for 2 to 3 weeks in a greenhouse. The required amount of the test compound was sprayed to the foliage of the test plants over the top by means of a small hand sprayer. After the spraying, the test plants were grown for further 3 weeks in the greenhouse, and herbicidal activity was examined. The results are shown in Table 2. In the above foliar application, the test compounds were each formulated into an emulsifiable concentrate, and the required amount of the emulsifiable concentrate was dispersed in water for application at a spray volume of 5 liters per are and applied with the addition of a wetting agent.

TABLE 2

| Compound No. | Dosage (weight of active ingredient, g/are) | Herbicidal activity Barnyard grass | Wild oat | Radish | Cucumber |
|---|---|---|---|---|---|
| 1 | 40 | 4 | 5 | 5 | 4 |
|  | 20 | 3 | 5 | 4 | 4 |
| 2 | 40 | 4 | 5 | 5 | 4 |
|  | 20 | 3 | 5 | 4 | 4 |
| 3 | 40 | 4 | 5 | 5 | 4 |
|  | 20 | 3 | 5 | 4 | 4 |
| 4 | 40 | 5 | 5 | 4 | 4 |
|  | 20 | 4 | 4 | 4 | 4 |
| 5 | 40 | 4 | 5 | 4 | 4 |
|  | 20 | 4 | 4 | 4 | 4 |
| 6 | 40 | 4 | 5 | 4 | 4 |
|  | 20 | 4 | 4 | 3 | 3 |
| 7 | 40 | 4 | 5 | 4 | 4 |
|  | 20 | 4 | 4 | 3 | 3 |
| 8 | 40 | 4 | 5 | 4 | 3 |
|  | 20 | 4 | 4 | 3 | 3 |
| 9 | 40 | 4 | 5 | 4 | 5 |
|  | 20 | 4 | 4 | 3 | 3 |
| 10 | 40 | 4 | 5 | 4 | 4 |
|  | 20 | 4 | 4 | 3 | 3 |
| 11 | 40 | 4 | 5 | 4 | 4 |
|  | 20 | 3 | 4 | 3 | 3 |
| 12 | 40 | 4 | 5 | 4 | 5 |
|  | 20 | 4 | 4 | 3 | 5 |
| 13 | 40 | 4 | 5 | 3 | 3 |
|  | 20 | 3 | 4 | 3 | 3 |
| 14 | 40 | 4 | 5 | 3 | 3 |
|  | 20 | 3 | 4 | 3 | 3 |
| 15 | 40 | 4 | 5 | 3 | 4 |
|  | 20 | 3 | 4 | 3 | 3 |
| 16 | 40 | 4 | 5 | 4 | 3 |
|  | 20 | 3 | 4 | 3 | 3 |
| 17 | 40 | 4 | 5 | 4 | 3 |
|  | 20 | 3 | 4 | 3 | 3 |
| 18 | 40 | 4 | 5 | 3 | 3 |
|  | 20 | 3 | 4 | 3 | 3 |
| 19 | 40 | 4 | 5 | 4 | 4 |
|  | 20 | 3 | 4 | 3 | 3 |
| 20 | 40 | 4 | 5 | 4 | 4 |
|  | 20 | 3 | 4 | 3 | 3 |
| 21 | 40 | 4 | 5 | 4 | 4 |
|  | 20 | 3 | 4 | 3 | 3 |
| 22 | 40 | 4 | 5 | 3 | 3 |
|  | 20 | 3 | 4 | 3 | 3 |
| 23 | 40 | 4 | 5 | 4 | 4 |
|  | 20 | 3 | 4 | 3 | 3 |
| 24 | 40 | 4 | 5 | 4 | 4 |
|  | 20 | 3 | 4 | 3 | 3 |
| 25 | 40 | 4 | 5 | 4 | 4 |
|  | 20 | 3 | 4 | 3 | 3 |
| 26 | 40 | 4 | 5 | 4 | 4 |
|  | 20 | 3 | 4 | 3 | 3 |
| 27 | 40 | 4 | 5 | 4 | 4 |
|  | 20 | 3 | 4 | 3 | 3 |
| 28 | 40 | 4 | 5 | 4 | 3 |
|  | 20 | 3 | 4 | 3 | 3 |
| 29 | 40 | 4 | 5 | 4 | 4 |
|  | 20 | 3 | 4 | 3 | 3 |
| 30 | 40 | 4 | 5 | 4 | 4 |
|  | 20 | 4 | 4 | 3 | 3 |
| 31 | 40 | 4 | 5 | 4 | 3 |
|  | 20 | 4 | 4 | 3 | 3 |
| 32 | 40 | 4 | 5 | 4 | 4 |
|  | 20 | 3 | 5 | 3 | 3 |
| 33 | 40 | 4 | 5 | 4 | 3 |
|  | 20 | 4 | 4 | 3 | 3 |
| 34 | 40 | 4 | 5 | 4 | 3 |
|  | 20 | 4 | 4 | 3 | 3 |
| 35 | 40 | 4 | 5 | 4 | 4 |
|  | 20 | 3 | 4 | 3 | 3 |
| 36 | 40 | 4 | 5 | 4 | 4 |
|  | 20 | 4 | 4 | 3 | 3 |
| 37 | 40 | 4 | 5 | 4 | 4 |
|  | 20 | 3 | 4 | 3 | 3 |
| 38 | 40 | 4 | 5 | 4 | 4 |
|  | 20 | 3 | 4 | 3 | 3 |

TABLE 2-continued

| Compound No. | Dosage (weight of active ingredient, g/are) | Herbicidal activity Barnyard grass | Wild oat | Radish | Cucumber |
|---|---|---|---|---|---|
| 39 | 40 | 5 | 5 | 4 | 4 |
|  | 20 | 4 | 4 | 3 | 3 |
| 40 | 40 | 4 | 5 | 3 | 3 |
|  | 20 | 4 | 4 | 3 | 3 |
| 41 | 40 | 4 | 4 | 4 | 3 |
|  | 20 | 3 | 4 | 3 | 3 |
| 42 | 40 | 4 | 4 | 4 | 3 |
|  | 20 | 3 | 4 | 3 | 3 |
| 43 | 40 | 3 | 4 | 3 | 3 |
|  | 20 | 3 | 4 | 3 | 3 |
| 44 | 40 | 4 | 4 | 3 | 3 |
|  | 20 | 3 | 4 | 3 | 3 |
| 45 | 40 | 4 | 5 | 5 | 3 |
|  | 20 | 3 | 4 | 4 | 3 |
| 46 | 40 | 4 | 5 | 3 | 3 |
|  | 20 | 3 | 4 | 3 | 3 |
| 47 | 40 | 4 | 5 | 3 | 3 |
|  | 20 | 3 | 5 | 3 | 3 |
| 48 | 40 | 3 | 4 | 4 | 3 |
|  | 20 | 3 | 4 | 3 | 3 |
| 49 | 40 | 4 | 5 | 5 | 5 |
|  | 20 | 3 | 4 | 4 | 5 |
| 50 | 40 | 3 | 5 | 3 | 5 |
|  | 20 | 3 | 4 | 3 | 5 |
| 51 | 40 | 4 | 4 | 3 | 4 |
|  | 20 | 3 | 4 | 3 | 3 |
| 52 | 40 | 4 | 4 | 3 | 3 |
|  | 20 | 3 | 4 | 3 | 3 |
| 53 | 40 | 4 | 5 | 3 | 3 |
|  | 20 | 3 | 5 | 3 | 3 |
| 54 | 40 | 3 | 4 | 3 | 3 |
|  | 20 | 3 | 4 | 3 | 3 |
| 55 | 40 | 4 | 4 | 3 | 3 |
|  | 20 | 4 | 4 | 3 | 3 |
| 56 | 40 | 3 | 4 | 3 | 3 |
|  | 20 | 3 | 4 | 3 | 3 |
| 57 | 40 | 5 | 5 | 3 | 3 |
|  | 20 | 4 | 5 | 3 | 3 |
| 58 | 40 | 4 | 5 | 3 | 3 |
|  | 20 | 4 | 5 | 3 | 3 |
| 59 | 40 | 3 | 5 | 3 | 3 |
|  | 20 | 3 | 5 | 3 | 3 |
| 60 | 40 | 3 | 5 | 3 | 3 |
|  | 20 | 3 | 4 | 3 | 3 |
| 61 | 40 | 3 | 5 | 4 | 3 |
|  | 20 | 3 | 4 | 3 | 3 |
| 62 | 40 | 4 | 4 | 3 | 3 |
|  | 20 | 4 | 4 | 3 | 3 |
| 63 | 40 | 3 | 5 | 4 | 3 |
|  | 20 | 3 | 4 | 3 | 3 |
| 64 | 40 | 3 | 5 | 3 | 3 |
|  | 20 | 3 | 4 | 3 | 3 |
| 65 | 40 | 3 | 4 | 3 | 3 |
|  | 20 | 3 | 4 | 3 | 3 |
| 66 | 40 | 4 | 4 | 4 | 4 |
|  | 20 | 3 | 4 | 3 | 3 |
| 67 | 40 | 4 | 4 | 4 | 3 |
|  | 20 | 3 | 4 | 4 | 3 |
| 68 | 40 | 3 | 5 | 4 | 3 |
|  | 20 | 3 | 4 | 4 | 3 |
| 69 | 40 | 4 | 4 | 4 | 4 |
|  | 20 | 3 | 4 | 4 | 3 |
| 70 | 40 | 4 | 4 | 3 | 3 |
|  | 20 | 4 | 4 | 3 | 3 |
| 71 | 40 | 4 | 5 | 4 | 3 |
|  | 20 | 4 | 4 | 4 | 3 |
| 72 | 40 | 3 | 5 | 3 | 3 |
|  | 20 | 3 | 4 | 3 | 3 |
| 73 | 40 | 5 | 5 | 3 | 3 |
|  | 20 | 4 | 4 | 3 | 3 |
| 74 | 40 | 5 | 5 | 3 | 3 |
|  | 20 | 4 | 4 | 3 | 3 |
| 75 | 40 | 4 | 4 | 4 | 5 |
|  | 20 | 4 | 4 | 3 | 5 |
| 76 | 40 | 4 | 5 | 3 | 3 |
|  | 20 | 4 | 4 | 3 | 3 |
| 77 | 40 | 4 | 5 | 3 | 3 |
|  | 20 | 3 | 4 | 3 | 3 |
| 78 | 40 | 4 | 4 | 4 | 5 |
|  | 20 | 4 | 4 | 3 | 4 |
| 79 | 40 | 5 | 5 | 3 | 3 |
|  | 20 | 4 | 4 | 3 | 3 |
| 80 | 40 | 3 | 5 | 3 | 4 |
|  | 20 | 3 | 4 | 3 | 3 |
| 81 | 40 | 4 | 4 | 4 | 4 |
|  | 20 | 4 | 4 | 3 | 3 |
| 82 | 40 | 4 | 4 | 4 | 4 |
|  | 20 | 4 | 3 | 4 | 4 |
| 83 | 40 | 4 | 4 | 4 | 4 |
|  | 20 | 3 | 4 | 4 | 3 |
| 84 | 40 | 4 | 4 | 4 | 4 |
|  | 20 | 4 | 4 | 3 | 4 |
| 85 | 40 | 3 | 4 | 3 | 4 |
|  | 20 | 3 | 4 | 3 | 3 |
| 86 | 40 | 3 | 4 | 3 | 4 |
|  | 20 | 3 | 4 | 3 | 3 |
| 87 | 40 | 3 | 4 | 3 | 3 |
|  | 20 | 3 | 4 | 3 | 3 |
| 88 | 40 | 3 | 4 | 3 | 4 |
|  | 20 | 3 | 4 | 3 | 4 |
| 89 | 40 | 3 | 4 | 3 | 4 |
|  | 20 | 3 | 4 | 3 | 4 |
| 90 | 40 | 4 | 4 | 3 | 5 |
|  | 20 | 3 | 4 | 3 | 4 |
| 91 | 40 | 3 | 4 | 3 | 5 |
|  | 20 | 3 | 3 | 3 | 4 |
| 92 | 40 | 3 | 4 | 3 | 4 |
|  | 20 | 3 | 3 | 3 | 3 |
| 93 | 40 | 3 | 4 | 3 | 4 |
|  | 20 | 3 | 4 | 3 | 4 |
| 94 | 40 | 3 | 5 | 3 | 4 |
|  | 20 | 3 | 4 | 3 | 3 |
| 95 | 40 | 4 | 5 | 5 | 4 |
|  | 20 | 3 | 5 | 4 | 3 |
| 96 | 40 | 4 | 5 | 5 | 4 |
|  | 20 | 3 | 5 | 4 | 3 |
| 97 | 40 | 5 | 5 | 4 | 4 |
|  | 20 | 4 | 5 | 4 | 4 |
| 98 | 40 | 4 | 5 | 5 | 4 |
|  | 20 | 3 | 4 | 4 | 3 |
| 99 | 40 | 4 | 5 | 3 | 4 |
|  | 20 | 3 | 4 | 3 | 3 |
| 100 | 40 | 3 | 5 | 3 | 4 |
|  | 20 | 3 | 4 | 3 | 3 |
| 101 | 40 | 3 | 5 | 4 | 4 |
|  | 20 | 3 | 5 | 3 | 3 |
| Control (a) | 40 | 0 | 2 | 0 | 0 |
|  | 20 | 0 | 1 | 0 | 0 |
| Control (c) | 40 | 2 | 2 | 0 | 0 |
|  | 20 | 1 | 1 | 0 | 0 |

EXAMPLE 22

Pre-emergence application:-

Plastic trays (35 cm×25 cm×10 cm (high)) were filled with upland field soil, and the seeds of cotton, annual morningglory, redroot pigweed, rice plant, barnyard grass, wheat, wild oat, sugarbeet, green foxtail, common lambsquarters and bedstraw were separately sowed in the trays. The required amount of a wettable powder was dispersed in water so as to make the active ingredient 40 grams per are and sprayed at a volume of 5 liters per are to the whole surface of the soil by means of a small hand sprayer. After the spraying, the trans were placed in a greenhouse for 20 days, the phytotoxicity and herbicidal activity were examined. The results are shown in Table 3.

TABLE 3

| Compound No. | Phytotoxicity | | | | Herbicidal activity | | | | | | |
|---|---|---|---|---|---|---|---|---|---|---|---|
| | Cotton | Rice plant | Wheat | Sugar-beet | Annual morning-glory | Redroot pigweed | Barnyard grass | Wild oat | Green foxtail | Common lambsquarters | Bedstraw |
| 1 | 0 | 0 | 0 | 1 | 5 | 4 | 4 | 4 | 4 | 5 | — |
| 2 | 0 | 0 | 0 | 1 | 5 | 4 | 4 | 4 | 4 | 5 | — |
| 3 | 0 | 0 | 0 | 1 | 5 | 4 | 4 | 4 | 4 | 5 | — |
| 4 | 0 | 0 | 1 | 1 | 5 | 5 | 5 | 4 | 4 | 5 | 4 |
| 5 | 0 | 0 | 1 | 1 | 5 | 5 | 5 | 4 | 4 | 5 | 4 |
| 6 | 0 | 0 | 0 | 0 | 5 | 5 | 5 | 4 | 4 | 5 | 4 |
| 7 | 0 | 0 | 0 | 0 | 4 | 5 | 5 | 4 | 3 | 4 | — |
| 8 | 0 | 0 | 0 | 0 | 4 | 5 | 5 | 4 | 4 | 4 | — |
| 9 | 0 | 0 | 0 | 0 | 3 | 5 | 4 | 4 | 3 | 4 | — |
| 10 | 0 | 0 | 0 | 0 | 4 | 5 | 5 | 5 | 4 | 4 | — |
| 11 | 0 | 0 | 0 | 0 | 4 | 5 | 5 | 4 | 4 | 4 | — |
| 12 | 0 | 0 | 0 | 0 | 3 | 5 | 5 | 4 | 4 | 4 | — |
| 13 | 0 | 0 | 0 | 0 | 4 | 3 | 4 | 4 | 3 | 4 | — |
| 14 | 0 | 0 | 0 | 0 | 4 | 4 | 4 | 4 | 4 | 4 | — |
| 15 | 0 | 0 | 0 | 0 | 4 | 5 | 5 | 5 | 4 | 3 | — |
| 16 | 0 | 0 | 0 | 0 | 4 | 5 | 5 | 5 | 4 | 3 | — |
| 17 | 0 | 0 | 0 | 0 | 5 | 5 | 5 | 5 | 3 | 4 | — |
| 18 | 0 | 0 | 0 | 0 | 4 | 5 | 4 | 4 | 3 | 4 | — |
| 19 | 0 | 0 | 0 | 0 | 4 | 5 | 5 | 4 | 3 | 4 | — |
| 20 | 0 | 0 | 0 | 0 | 5 | 5 | 5 | 5 | 4 | 4 | — |
| 21 | 0 | 0 | 0 | 0 | 4 | 4 | 5 | 4 | 4 | 3 | — |
| 22 | 0 | 0 | 0 | 0 | 4 | 5 | 5 | 4 | 4 | 4 | — |
| 23 | 0 | 0 | 0 | 0 | 4 | 4 | 4 | 4 | 4 | 4 | — |
| 24 | 0 | 0 | 0 | 0 | 4 | 4 | 5 | 4 | 4 | 3 | — |
| 25 | 0 | 0 | 0 | 0 | 4 | 4 | 4 | 4 | 4 | 4 | — |
| 26 | 0 | 0 | 0 | 0 | 4 | 4 | 5 | 4 | 4 | 3 | — |
| 27 | 0 | 0 | 0 | 0 | 4 | 4 | 4 | 5 | 4 | 3 | — |
| 28 | 0 | 0 | 0 | 0 | 4 | 4 | 5 | 5 | 4 | 3 | — |
| 29 | 0 | 0 | 0 | 0 | 4 | 4 | 5 | 5 | 4 | 4 | — |
| 30 | 0 | 0 | 0 | 0 | 4 | 5 | 5 | 5 | 4 | 4 | — |
| 31 | 0 | 0 | 0 | 0 | 4 | 5 | 4 | 4 | 4 | 4 | — |
| 32 | 0 | 0 | 0 | 0 | 4 | 5 | 5 | 4 | 4 | 4 | — |
| 33 | 0 | 0 | 0 | 0 | 4 | 4 | 4 | 4 | 3 | 3 | — |
| 34 | 0 | 0 | 0 | 0 | 4 | 4 | 4 | 5 | 3 | 3 | — |
| 35 | 0 | 0 | 0 | 0 | 4 | 5 | 5 | 4 | 4 | 4 | — |
| 36 | 0 | 0 | 0 | 0 | 1 | 4 | 4 | 5 | 4 | 4 | — |
| 37 | 0 | 0 | 0 | 0 | 4 | 4 | 4 | 5 | 4 | 4 | — |
| 38 | 0 | 0 | 0 | 0 | 5 | 4 | 5 | 5 | 5 | 4 | — |
| 39 | 0 | 0 | 0 | — | 4 | 4 | 4 | 4 | 4 | — | — |
| 40 | 0 | 0 | 0 | 0 | 5 | 5 | 5 | 5 | 4 | 4 | — |
| 41 | 0 | 0 | 0 | 0 | 3 | 5 | 5 | 4 | 4 | 4 | — |
| 42 | 0 | 0 | 0 | 1 | 3 | 5 | 5 | 4 | 4 | 5 | — |
| 43 | 0 | 0 | 0 | 0 | 3 | 4 | 4 | 4 | 4 | 5 | — |
| 44 | 0 | 0 | 0 | 0 | 3 | 4 | 4 | 4 | 4 | 4 | — |
| 45 | 0 | 0 | 0 | 0 | 4 | 5 | 5 | 5 | 5 | 5 | — |
| 46 | 0 | 0 | 0 | 1 | 3 | 5 | 5 | 4 | 5 | 5 | — |
| 47 | 0 | 0 | 0 | 0 | 5 | 5 | 5 | 5 | 5 | 5 | — |
| 48 | 0 | 0 | 0 | 0 | 3 | 4 | 4 | 4 | 4 | 5 | — |
| 49 | 0 | 0 | 0 | 0 | 4 | 4 | 5 | 4 | 4 | 4 | — |
| 50 | 0 | 0 | 0 | 0 | 4 | 5 | 4 | 4 | 4 | 5 | — |
| 51 | 0 | 0 | 0 | 1 | 5 | 5 | 4 | 4 | 5 | 5 | — |
| 52 | 0 | 0 | 1 | 1 | 4 | 5 | 4 | 4 | 5 | 5 | — |
| 53 | 0 | 0 | 0 | 0 | 4 | 5 | 5 | 5 | 5 | 5 | — |
| 54 | 0 | 1 | 0 | 0 | 3 | 5 | 5 | 4 | 5 | 4 | — |
| 55 | 0 | 0 | 1 | 0 | 3 | 4 | 4 | 4 | 4 | 4 | — |
| 56 | 0 | 0 | 0 | 0 | 4 | 4 | 5 | 4 | 5 | 4 | — |
| 57 | 0 | 0 | 0 | 0 | 5 | 5 | 5 | 4 | 5 | 5 | — |
| 58 | 0 | 0 | 0 | 0 | 5 | 5 | 4 | 4 | 4 | 4 | — |
| 59 | 0 | 1 | 0 | 1 | 5 | 5 | 4 | 4 | 4 | 5 | — |
| 60 | 0 | 0 | 0 | 1 | 4 | 5 | 4 | 4 | 4 | 5 | — |
| 61 | 0 | 0 | 0 | 0 | 5 | 5 | 5 | 4 | 5 | 4 | — |
| 62 | 0 | 0 | 1 | 1 | 4 | 4 | 4 | 4 | 5 | 5 | — |
| 63 | 0 | 1 | 0 | 0 | 4 | 5 | 4 | 4 | 5 | 4 | — |
| 64 | 0 | 0 | 0 | 0 | 5 | 5 | 5 | 4 | 4 | 5 | — |
| 65 | 0 | 1 | 0 | 1 | 4 | 4 | 4 | 4 | 4 | 5 | — |
| 66 | 0 | 0 | 1 | 0 | 4 | 4 | 4 | 4 | 5 | 4 | — |
| 67 | 0 | 0 | 0 | 0 | 4 | 5 | 4 | 4 | 5 | 4 | — |
| 68 | 0 | 0 | 0 | 0 | 4 | 5 | 4 | 5 | 4 | 5 | — |
| 69 | 0 | 0 | 0 | 0 | 4 | 5 | 4 | 4 | 5 | 5 | — |
| 70 | 0 | 0 | 0 | 0 | 4 | 5 | 4 | 5 | 5 | 4 | — |
| 71 | 0 | 0 | 0 | 0 | 4 | 4 | 4 | 4 | 4 | 4 | — |
| 72 | 0 | 1 | 0 | 1 | 4 | 4 | 4 | 4 | 4 | 5 | — |
| 73 | 0 | 0 | 0 | — | 4 | 5 | 4 | 4 | — | — | — |
| 74 | 0 | 0 | 0 | — | 4 | 5 | 4 | 4 | — | — | — |
| 75 | 0 | 1 | 0 | 1 | 4 | 4 | 4 | 4 | 3 | 4 | — |
| 76 | 0 | 0 | 0 | 0 | 5 | 5 | 3 | 4 | 3 | 4 | — |
| 77 | 0 | 1 | 0 | 1 | 4 | 4 | 4 | 4 | 4 | 5 | — |

TABLE 3-continued

| Compound No. | Phytotoxicity | | | | Herbicidal activity | | | | | | |
|---|---|---|---|---|---|---|---|---|---|---|---|
| | Cotton | Rice plant | Wheat | Sugar-beet | Annual morning-glory | Redroot pigweed | Barnyard grass | Wild oat | Green foxtail | Common lambsquarters | Bedstraw |
| 78 | 0 | 1 | 0 | — | 4 | 4 | 4 | 4 | — | — | — |
| 79 | 0 | 0 | 0 | 0 | 5 | 5 | 3 | 4 | 3 | 4 | — |
| 80 | 0 | 0 | 0 | 1 | 3 | 5 | 4 | 3 | 3 | 4 | — |
| 81 | 0 | 0 | 1 | — | 4 | 4 | 3 | 3 | — | — | — |
| 82 | 0 | 0 | 1 | 0 | 4 | 4 | 4 | 4 | 3 | 3 | — |
| 83 | 0 | 0 | 1 | 1 | 4 | 4 | 3 | 4 | 3 | 4 | — |
| 84 | 0 | 0 | 1 | — | 4 | 4 | 3 | 3 | — | — | — |
| 85 | 0 | 0 | 0 | 0 | 3 | 3 | 4 | 3 | 3 | 3 | — |
| 86 | 0 | 0 | 1 | 1 | 3 | 4 | 4 | 3 | 3 | 5 | — |
| 87 | 0 | 0 | 1 | — | 3 | 3 | 3 | 3 | — | — | — |
| 88 | 0 | 0 | 1 | — | 3 | 3 | 4 | 3 | — | — | — |
| 89 | 0 | 0 | 1 | — | 3 | 3 | 4 | 3 | — | — | — |
| 90 | 0 | 0 | 1 | — | 3 | 4 | 4 | 3 | — | — | — |
| 91 | 0 | 0 | 1 | 0 | 3 | 4 | 4 | 5 | 4 | 5 | — |
| 92 | 0 | 0 | 1 | 0 | 5 | 5 | 4 | 5 | 4 | 4 | — |
| 93 | 0 | 0 | 1 | 0 | 4 | 5 | 4 | 5 | 4 | 4 | — |
| 94 | 0 | 0 | 0 | 0 | 3 | 4 | 4 | 4 | 3 | 4 | — |
| 95 | 0 | 0 | 0 | 1 | 5 | 4 | 4 | 4 | 4 | 5 | — |
| 96 | 0 | 0 | 0 | 1 | 5 | 4 | 4 | 4 | 4 | 5 | — |
| 97 | 0 | 0 | 1 | 1 | 5 | 5 | 5 | 4 | 4 | 5 | 4 |
| 98 | 0 | 0 | 0 | 1 | 5 | 5 | 4 | 4 | 5 | 5 | — |
| 99 | 0 | 0 | 0 | 0 | 5 | 4 | 4 | 5 | 4 | 5 | — |
| 100 | 0 | 0 | 0 | 0 | 3 | 4 | 4 | 4 | 3 | 4 | — |
| 101 | 0 | 0 | 0 | 1 | 3 | 4 | 5 | 4 | 3 | 5 | — |
| Control (a) | 0 | 0 | 0 | 0 | 1 | 1 | 1 | 0 | 0 | 1 | — |
| Control (c) | 0 | 0 | 0 | 0 | 2 | 2 | 2 | 1 | 1 | 0 | — |

EXAMPLE 23

Post-emergence application (in cultivated field):-

Seeds of wheat, barley and wild oat were simultaneously sowed in one plot (1 m×1 m) of a cultivated field, and when wild oat grew up to 2-leaf stage and to 4-leaf stage, respectively, a required amount of the test compound was sprayed to the foliage of the test plants over the top by means of a small hand sprayer. After the spraying, the test plants were grown for further 5 weeks, and herbicidal activity and phytotoxicity were examined. The results are shown in Table 4. In the above foliar application, the test compounds were each formulated into an emulsifiable concentrate and the required amount of the emulsifiable concentrate was dispersed in water for application at a spray volume of 5 liters per are and applied with the addition of a wetting agent.

TABLE 4

| Compound No. | Dosage (weight of active ingredient, g/are) | Phytotoxicity | | | | Herbicidal activity | |
|---|---|---|---|---|---|---|---|
| | | Wheat | | Barley | | Wild oat | |
| | | 2-leaf stage | 4-leaf stage | 2-leaf stage | 4-leaf stage | 2-leaf stage | 4-leaf stage |
| 15 | 20 | 1 | 1 | 1 | 0 | 5 | 4 |
| | 10 | 0 | 0 | 1 | 0 | 4 | 3 |
| 20 | 20 | 1 | 1 | 1 | 1 | 5 | 4 |
| | 10 | 0 | 0 | 0 | 0 | 4 | 3 |
| 41 | 20 | 1 | 0 | 1 | 0 | 5 | 4 |
| | 10 | 0 | 0 | 0 | 0 | 4 | 3 |
| 56 | 20 | 1 | 1 | 1 | 1 | 5 | 4 |
| | 10 | 1 | 0 | 0 | 0 | 4 | 3 |
| 86 | 20 | 1 | 0 | 1 | 1 | 5 | 4 |
| | 10 | 0 | 0 | 1 | 0 | 4 | 3 |
| 95 | 20 | 1 | 0 | 1 | 1 | 5 | 4 |
| | 10 | 0 | 0 | 0 | 0 | 4 | 3 |
| 96 | 20 | 0 | 0 | 0 | 0 | 5 | 5 |
| | 10 | 0 | 0 | 0 | 0 | 4 | 4 |
| Control (a) | 20 | 0 | 0 | 0 | 0 | 1 | 0 |
| | 10 | 0 | 0 | 0 | 0 | 0 | 0 |
| Control (b) | 20 | 3 | 3 | 4 | 3 | 5 | 4 |
| | 10 | 2 | 2 | 3 | 2 | 4 | 3 |
| Control (c) | 20 | 0 | 0 | 0 | 0 | 2 | 1 |
| | 10 | 0 | 0 | 0 | 0 | 2 | 0 |
| Barban | 20 | 3 | 1 | 3 | 1 | 5 | 1 |
| | 10 | 3 | 0 | 3 | 0 | 4 | 0 |

What is claimed is:

1. A herbicidal composition which comprises as an active ingredient at least one of the 3,5-dioxo-1,2,4-triazine derivatives of the formula:

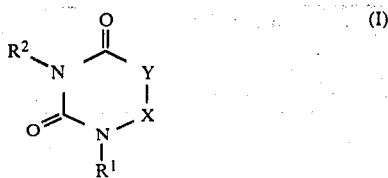 (I)

wherein
(1) (a) —X—Y— represents —N=CH—, (b) $R^1$ is a hydrogen atom, a hydroxylmethyl group, an aminomethyl group of the formula:

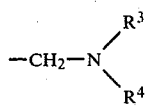

(in which $R^3$ and $R^4$ are each hydrogen, $C_1$–$C_{12}$ alkyl, allyl, propargyl, cyanoethyl, phenyl or $C_3$–$C_{10}$ cycloalkyl or, when taken together with the adjacent nitrogen atom, represent a 3 to 13-membered saturated nitrogen-containing heterocyclic group optionally containing an oxygen atom or an additional nitrogen atom and/or optionally bearing not more than three methyl or ethyl groups), an acyloxymethyl group of the formula:

—CH$_2$—OOC—$R^5$ (in which $R^5$ is $C_1$–$C_9$ alkyl, $C_2$–$C_5$ alkenyl, $C_2$–$C_5$ alkynyl or cyclohexyl, these $R^5$ groups being optionally substituted with not more than five halogen, $C_1$–$C_5$ alkoxy, phenyl or phenoxy groups, or phenyl, naphthyl, nicotinyl or isonicotinyl, these being optionally substituted with not more than five methyl, methoxy, halogen, nitro or trihalomethyl groups or with 3,4-methylenedioxy) or a cyclic ether group of the formula:

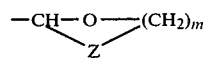

(in which Z is —CH$_2$CH$_2$— and m is an integer of 1 or 2 or Z is —CHX'CH$_2$—, —CHX'CHX'— or —CH=CH— (X' being halogen) and m is 1) and (c) $R^2$ is a hydrogen atom, an aminomethyl group of the formula:

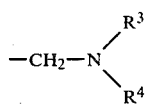

(in which $R^3$ and $R^4$ are each as defined above) or a cyclic ether group of the formula:

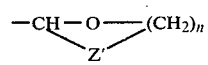

(in which Z' is —CH$_2$CH$_2$— and n is an integer of 1 or 2 or Z is —CHY'CH$_2$— (Y' being halogen) and n is 1), provided that when $R^2$ is a hydrogen atom, $R^1$ is a hydroxymethyl group, an acyloxymethyl group of the formula:

—CH$_2$—OOC—$R^5$ or a cyclic ether group of the formula:

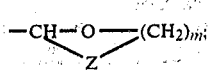

when $R^2$ is an aminomethyl group of the formula:

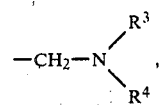

$R^1$ is an aminomethyl group of the formula:

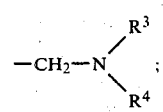

or when $R^2$ is a cyclic ether group of the formula:

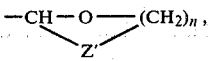

$R^1$ is a hydrogen atom or a group of the formula:

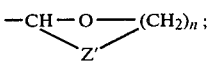

or
(2) (a) —X—Y— represents —NH—CH$_2$—, (b) $R^1$ is a hydrogen atom, an acyloxymethyl group of the formula:
—CH$_2$—OOC—$R^6$ (in which $R^6$ is $C_1$–$C_9$ alkyl, cyclohexyl or phenyl, these being optionally substituted with not more than five methyl, methoxy, fluorine, chlorine or trihalomethyl groups or with 3,4-methylenedioxy) or a cyclic ether group of the formula:

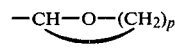

(in which p is an integer of 3 or 4) and (c) $R^2$ is a hydrogen atom or a cyclic ether group of the formula:

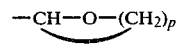

(in which p is as defined above), provided that when $R^2$ is a cyclic ether group of the formula:

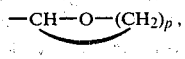

$R^1$ is a hydrogen atom or a cyclic ether group of the formula:

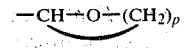

in the free or salt form in a herbicidally effective amount, and at least one inert carrier or diluent.

2. The composition according to claim 1, wherein the active ingredient is representable by the formula (I) wherein —X—Y— is —N=CH—, $R^1$ is

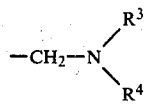

and $R^2$ is

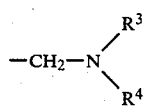

(in which $R^3$ and $R^4$ are each as defined in claim 1).

3. The composition according to claim 1, wherein the active ingredient is representable by the formula (I) wherein —X—Y— is —N=CH— and $R^1$ is —CH$_2$—OOC—$R^5$ (in which $R^5$ is as defined in claim 1).

4. The composition according to claim 1, wherein the active ingredient is representable by the formula (I) wherein —X—Y— is —N=CH—, $R^1$ is —H or

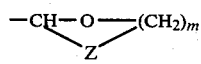

and $R^2$ is —H or

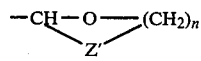

(in which Z, Z', m and n are each as defined in claim 1).

5. The composition according to claim 1, wherein the active ingredient is 2-hydroxymethyl-3,5-dioxo-2,3,4,5-tetrahydro-1,2,4-triazine or a salt thereof.

6. The composition according to claim 1, wherein the active ingredient is 3,5-dioxo-hexahydro-1,2,4-triazine or a salt thereof.

7. The composition according to claim 1, wherein the active ingredient is 2,4-bis(N-n-butyl-N-methylaminomethyl)-3,5-dioxo-2,3,4,5-tetrahydro-1,2,4-triazine.

8. The composition according to claim 1, wherein the active ingredient is 2,4-bis(N,N-dimethylaminomethyl)-3,5-dioxo-2,3,4,5-tetrahydro-1,2,4-triazine.

9. The composition according to claim 1, wherein the active ingredient is 2-(3-methylbenzoyloxymethyl)-3,5-dioxo-2,3,4,5-tetrahydro-1,2,4-triazine or a salt thereof.

10. The composition according to claim 1, wherein the active ingredient is 3,5-dioxo-4-(tetrahydro-2-furanyl)-2,3,4,5-tetrahydro-1,2,4-triazine or a salt thereof.

11. A method for exterminating wild oats, which comprises applying a herbicidally effective amount of at least one of the 3,5-dioxo-1,2,4-triazine derivatives as defined in claim 1 in the free or salt form to the area where it is desired to exterminate or control the wild oats.

12. The method according to claim 11, wherein the area of application is a field where wheat is cultivated.

13. A 3,5-dioxo-1,2,4-triazine derivative of the formula:

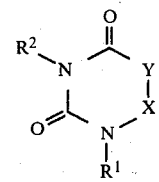

wherein (1) (a) —X—Y— represents —N=CH—, (b) $R^1$ is a hydrogen atom, a hydroxylmethyl group, an aminomethyl group of the formula:

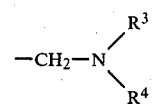

(in which $R^3$ and $R^4$ are each hydrogen, $C_1$-$C_{12}$ alkyl, allyl, propargyl, cyanoethyl, phenyl or $C_3$-$C_{10}$ cycloalkyl or, when taken together with the adjacent nitrogen atom, represent a 3 to 13-membered saturated nitrogen-containing heterocyclic group optionally containing an oxygen atom or an additional nitrogen atom and/or optionally bearing not more than three methyl or ethyl groups), an acyloxymethyl group of the formula:

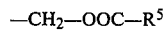

—CH$_2$—OOC—$R^5$ (in which $R^5$ is $C_1$-$C_9$ alkyl, $C_2$-$C_5$ alkenyl, $C_2$-$C_5$ alkynyl or cyclohexyl, these $R^5$ groups being optionally substituted with not more than five halogen, $C_1$-$C_5$ alkoxy, phenyl or phenoxy groups, or phenyl, naphthyl, nicotinyl or isonicotinyl, these being optionally substituted with not more than five methyl, methoxy, halogen, nitro or trihalomethyl groups or with 3,4-methylenedioxy) or a cyclic ether group of the formula:

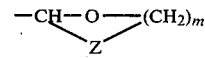

(in which Z is —CH$_2$CH$_2$— and m is an integer of 1 or 2 or Z is —CHX'CH$_2$—, —CHX'CHX'— or —CH=CH— (X' being halogen) and m is 1) and (c) $R^2$ is a hydrogen atom, an aminomethyl group of the formula:

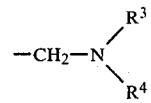

(in which $R^3$ and $R^4$ are each as defined above) or a cyclic ether group of the formula:

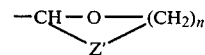

(in which Z' is —CH$_2$CH$_2$— and n is an integer of 1 or 2 or Z is —CHY'CH$_2$— (Y' being halogen) and n is 1), provided that when $R^2$ is a hydrogen atom, $R^1$ is a hydroxymethyl group, an acyloxymethyl group of the formula:

—CH$_2$OOC—R$^5$ or a cyclic ether group of the formula:

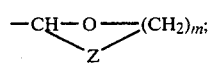

when R$^2$ is an aminomethyl group of the formula:

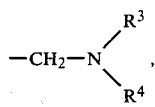

R$^1$ is an aminomethyl group of the formula:

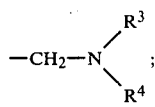

or when R$^2$ is a cyclic ether group of the formula:

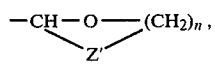

R$^1$ is a hydrogen atom or a group of the formula:

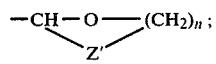

or (2) (a) —X—Y— represents —NH—CH$_2$—, (b) R$^1$ is a hydrogen atom, an acyloxymethyl group of the formula:

—CH$_2$—OOC—R$^6$ (in which R$^6$ is C$_1$–C$_9$ alkyl, cyclohexyl or phenyl, these being optionally substituted with not more than five methyl, methoxy, fluorine, chlorine or trihalomethyl groups or with 3,4-methylenedioxy) or a cyclic ether group of the formula:

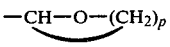

(in which p is an integer of 3 or 4) and (c) R$^2$ is a hydrogen atom or a cyclic ether group of the formula:

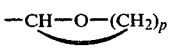

(in which p is as defined above), provided that when R$^2$ is a cyclic ether group of the formula:

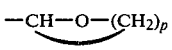

R$^1$ is a hydrogen atom or a cyclic ether of the formula:

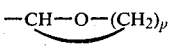

except the following cases:

(a) —X—Y— is —N=CH—, R$^1$ is hydroxymethyl and R$^2$ is a potassium atom;

(b) —X—Y— is —N=CH—, R$^1$ is hydroxymethyl and R$^2$ is a hydrogen atom;

(c) —X—Y— is —N=CH—, R$^1$ is

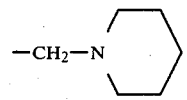

and R$^2$ is

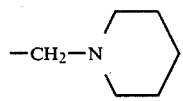

(d) —X—Y— is —N=CH—, R$^1$ is —CH$_2$—OOC—CH$_3$ and R$^2$ is a hydrogen atom;

(e) —X—Y— is —N=CH—, R$^1$ is

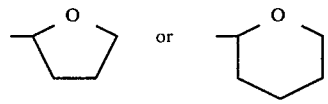

and R$^2$ is a hydrogen atom; and (f) —X—Y— is —NH—CH$_2$—, R$^1$ is a hydrogen atom and R$^2$ is a hydrogen atom, or a salt thereof.

14. The 3,5-dioxo-1,2,4-triazine derivative according to claim 13, wherein —X—Y— is —N=CH—, R$^1$ is

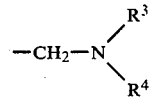

and R$^2$ is

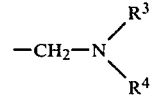

(in which R$^3$ and R$^4$ are each as defined in claim 11).

15. The 3,5-dioxo-1,2,4-triazine derivative according to claim 13, wherein —X—Y— is —N=CH— and R$^1$ is —CH$_2$—OOC—R$^5$ (in which R$^5$ is as defined in claim 11).

16. The 3,5-dioxo-1,2,4-triazine derivative according to claim 13, wherein —X—Y— is —N=CH—, R$^1$ is —H or

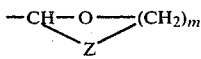

and R$^2$ is —H or

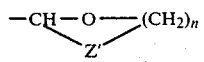

(in which Z, Z', m and n are each as defined in claim 11).

17. The 3,5-dioxo-1,2,4-triazine derivative 2,4-bis(N-n-butyl-N-methylaminomethyl-3,5-dioxo-2,3,4,5-tetrahydro-1,2,4-triazine.

18. The 3,5-dioxo-1,2,4-triazine derivative 2,4-bis(N,N-dimethylaminomethyl)-3,5-dioxo-2,3,4,5-tetrahydro-1,2,4-triazine.

19. The 3,5-dioxo-1,2,4-triazine derivative 2-(3-methylbenzoyloxymethyl)-3,5-dioxo-2,3,4,5-tetrahydro-1,2,4-triazine, or a salt thereof.

20. The 3,5-dioxo-1,2,4-triazine derivative 3,5-dioxo-4-(tetrahydro-2-furanyl)-2,3,4,5-tetrahydro-1,2,4-triazine, or a salt thereof.

* * * * *